United States Patent
Kobayashi

(10) Patent No.: US 8,258,457 B2
(45) Date of Patent: Sep. 4, 2012

(54) SCANNING ENDOSCOPE HAVING AN ACTUATOR AND A FORCE TRANSMITTER FOR BENDING A LIGHT TRANSMITTER

(75) Inventor: Shotaro Kobayashi, Tokyo (JP)

(73) Assignee: Hoya Corporation, Tokyo (JP)

(*) Notice: Subject to any disclaimer, the term of this patent is extended or adjusted under 35 U.S.C. 154(b) by 407 days.

(21) Appl. No.: 12/685,003

(22) Filed: Jan. 11, 2010

(65) Prior Publication Data

US 2010/0177368 A1 Jul. 15, 2010

(30) Foreign Application Priority Data

Jan. 13, 2009 (JP) ................. 2009-005109

(51) Int. Cl.
  *G01J 1/04* (2006.01)
(52) U.S. Cl. .................. 250/227.11; 250/234
(58) Field of Classification Search ............ 250/227.11, 250/227.16, 227.26, 234, 231.1; 385/31–33, 385/12, 13, 25, 91; 600/178, 129, 130, 476
See application file for complete search history.

(56) References Cited

U.S. PATENT DOCUMENTS 5,131,380 A * 7/1992 Heller et al. .............. 604/524
6,294,775 B1 9/2001 Seibel et al.
2007/0035797 A1 2/2007 Kanai

OTHER PUBLICATIONS

U.S. Appl. No. 12/685,109 to Kobayashi, which was filed on Jan. 11, 2010.

* cited by examiner

*Primary Examiner* — Que T Le
(74) *Attorney, Agent, or Firm* — Greenblum & Bernstein, P.L.C.

(57) ABSTRACT

A scanning endoscope comprising a light transmitter, an actuator, and a force transmitter, is provided. The light transmitter emits a beam of the light exiting the first emission end. The light transmitter is flexible. A longitudinal direction of the light transmitter is a first direction. The actuator is mounted near the first emission end. The actuator bends the light transmitter in a second direction by pushing a side of the light transmitter in the second direction. The second direction is perpendicular to the first direction. A force transmitter is oriented lengthwise in the first direction. The force transmitter is elastic. The force transmitter is positioned between the light transmitter and the actuator. The force transmitter exerts a pushing force supplied by the actuator on the side of the light transmitter while the force transmitter is deformed elastically toward the first direction.

17 Claims, 26 Drawing Sheets

FIG.6
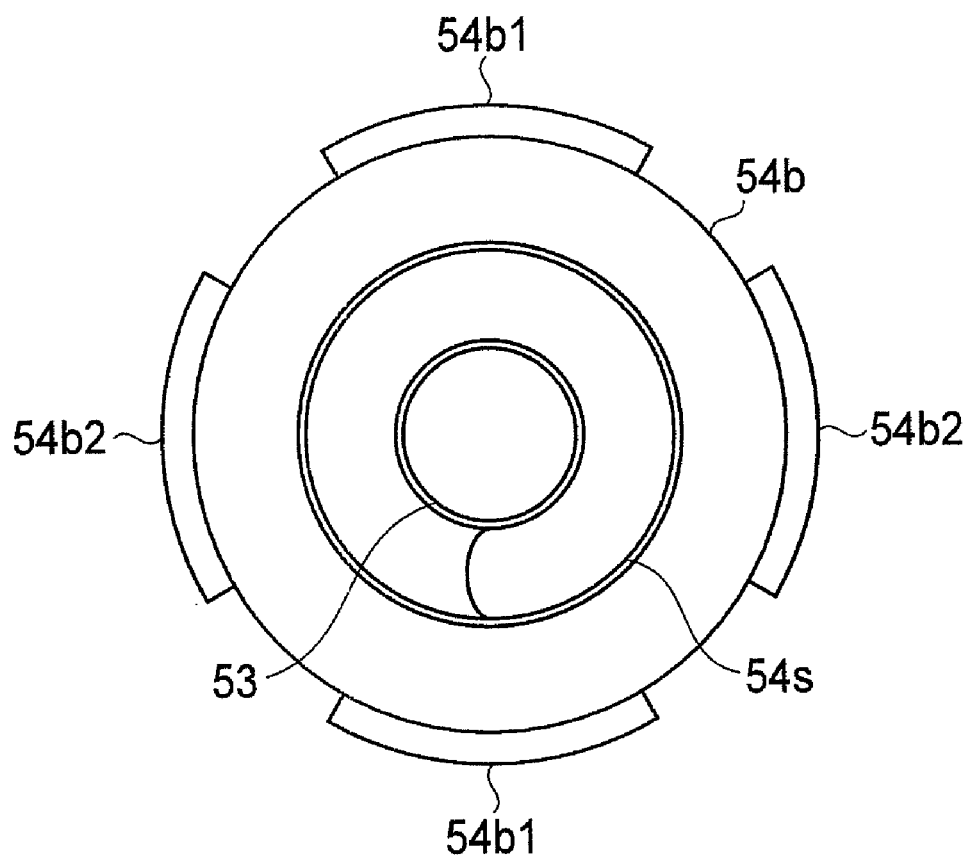
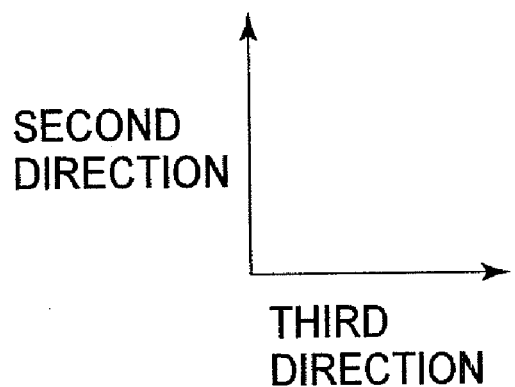

SCANNING ENDOSCOPE HAVING AN ACTUATOR AND A FORCE TRANSMITTER FOR BENDING A LIGHT TRANSMITTER

BACKGROUND OF THE INVENTION

1. Field of the Invention

The present invention relates to simplifying a manufacturing method and improving the accuracy of manufacturing an actuator that moves a fiber of a scanning endoscope.

2. Description of the Related Art

U.S. Pat. No. 6,294,775 discloses a scanning endoscope, which photographs and/or films an optical image of an observation area by scanning the observation area with light shined on a minute point in the area and successively capturing reflected light at the illuminated points. In a general scanning endoscope, light for illumination is transmitted through an optical fiber from a stationary incident end to a movable emission end and a scanning operation is carried out by successively moving the emission end of the optical fiber.

The structure of the emission end of an optical fiber in a general scanning endoscope is explained using FIG. 26. As shown in FIG. 26, the actuator 54' is mounted near an emission end of an illumination fiber 53'. The fiber actuator 54' comprises a bending block 54'b and a support block 54's.

The bending block 54'b is shaped cylindrically. The illumination fiber 53' is inserted through the cylindrical bending block 54'b. The illumination fiber 53' is supported at the forward end of the bending block 54'b by the supporting block 54's.

The supporting block 54's is shaped as a right circular cone so that the angle between a generatrix line and the base is 45 degrees. By shaping the supporting block 54's in this manner, the illumination fiber 53' can be repeatedly bent without breaking by a bending motion of the bending block 54'b that is transmitted through the supporting block 54's.

In order to form the supporting block 54's in the above-mentioned shape, when the illumination fiber 53' is inserted through the bending block 54'b, an adhesive is applied to the forward end of the bending block 54'b, and before it solidifies an operator transforms the adhesive to a right circular cone by vibrating the illumination fiber 53' along the axial direction of the bending block 54'b. The supporting block 54's is formed by the transformed adhesive solidifying as such a shape.

In the above manufacturing method it is difficult to adjust the length of the illumination fiber 53' that protrudes from the bending block 54'b. It is also difficult to accurately shape the supporting block 54's in the form of a right circular cone by the above-manufacturing method. As a result, increasing the yield of manufactured parts within required tolerance levels is difficult.

SUMMARY OF THE INVENTION

Therefore, an object of the present invention is to improve a manufacturing yield by making a bending block to support the illumination fiber so that the illumination fiber can sufficiently withstand the movements required of it during scanning.

According to the present invention, a scanning endoscope, comprising a light transmitter, an actuator, and a force transmitter, is provided. The light transmitter transmits light received at a first incident end to a first emission end. The light transmitter emits a beam of the light exiting the first emission end. The light transmitter is flexible. A longitudinal direction of the light transmitter is a first direction. The actuator is mounted near the first emission end. The actuator bends the light transmitter in a second direction by pushing a side of the light transmitter in the second direction. The second direction is perpendicular to the first direction. A force transmitter is oriented lengthwise in the first direction. The force transmitter is elastic. The force transmitter is positioned between the light transmitter and the actuator. The force transmitter exerts a pushing force supplied by the actuator on the side of the light transmitter while the force transmitter is deformed elastically toward the first direction.

BRIEF DESCRIPTION OF THE DRAWINGS

The objects and advantages of the present invention will be better understood from the following description, with reference to the accompanying drawings in which:

FIG. 6 is a front view of the fiber actuator in the first embodiment as seen from the emission end of the illumination fiber;

DESCRIPTION OF THE PREFERRED EMBODIMENTS

Figure 1:
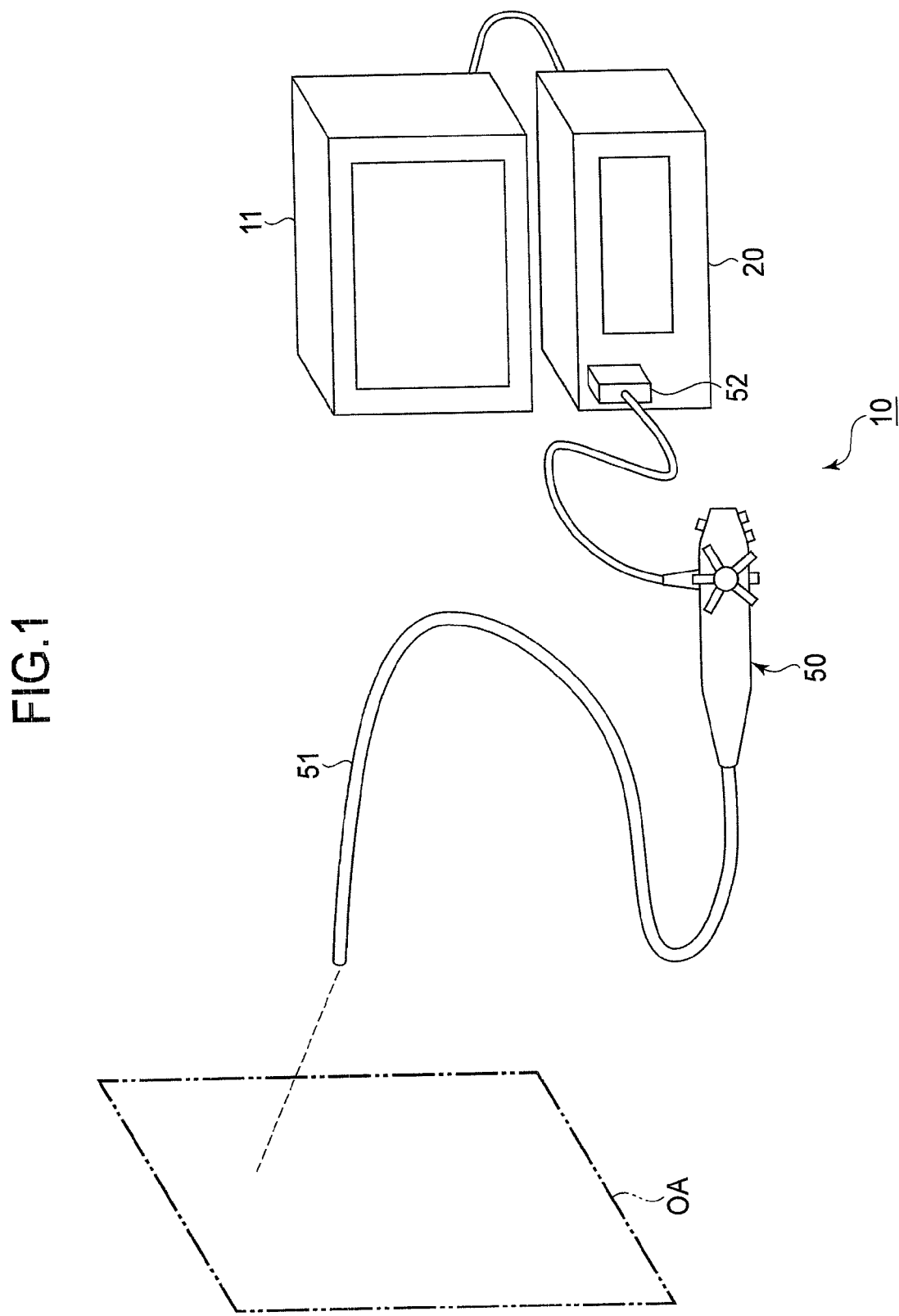
FIG. 1 is a schematic illustration of a scanning endoscope apparatus comprising a scanning endoscope of the first to seventh embodiments of the present invention.

The present invention is described below with reference to the embodiment shown in the drawings.

In FIG. 1, the scanning endoscope apparatus 10 comprises a scanning endoscope processor 20, a scanning endoscope 50, and a monitor 11. The scanning endoscope processor 20 is connected to the scanning endoscope 50 and the monitor 11.

Hereinafter, an emission end of an illumination fiber (not depicted in FIG. 1) and incident ends of image fibers (not depicted in FIG. 1) are ends mounted in the distal end of the insertion tube 51 of the scanning endoscope 50. In addition, an incident end of the illumination fiber (first incident end) and emission ends of the image fibers are ends mounted in a connector 52 that connects to the scanning endoscope processor 20.

The scanning endoscope processor 20 provides light that is shined on an observation area (see "OA" in FIG. 1). The light emitted from the scanning endoscope processor 20 is transmitted to the distal end of the insertion tube 51 through the illumination fiber (light transmitter), and is directed towards one point in the observation area. Light reflected from the illuminated point is transmitted from the distal end of the insertion tube 51 to the scanning endoscope processor 20.

The direction of the emission end of the illumination fiber (first emission end) is changed by a fiber actuator (not depicted in FIG. 1). By changing the direction, the observation area is scanned with the light emitted from the illumination fiber. The fiber actuator is controlled by the scanning endoscope processor 20.

The scanning endoscope processor 20 receives reflected light that is scattered at the illuminated point, and generates a pixel signal according to the amount of received light. One frame of an image signal is generated by generating pixel signals corresponding to the illuminated points dispersed throughout the observation area. The generated image signal is transmitted to the monitor 11, where an image corresponding to the received image signal is displayed.

Figure 2:
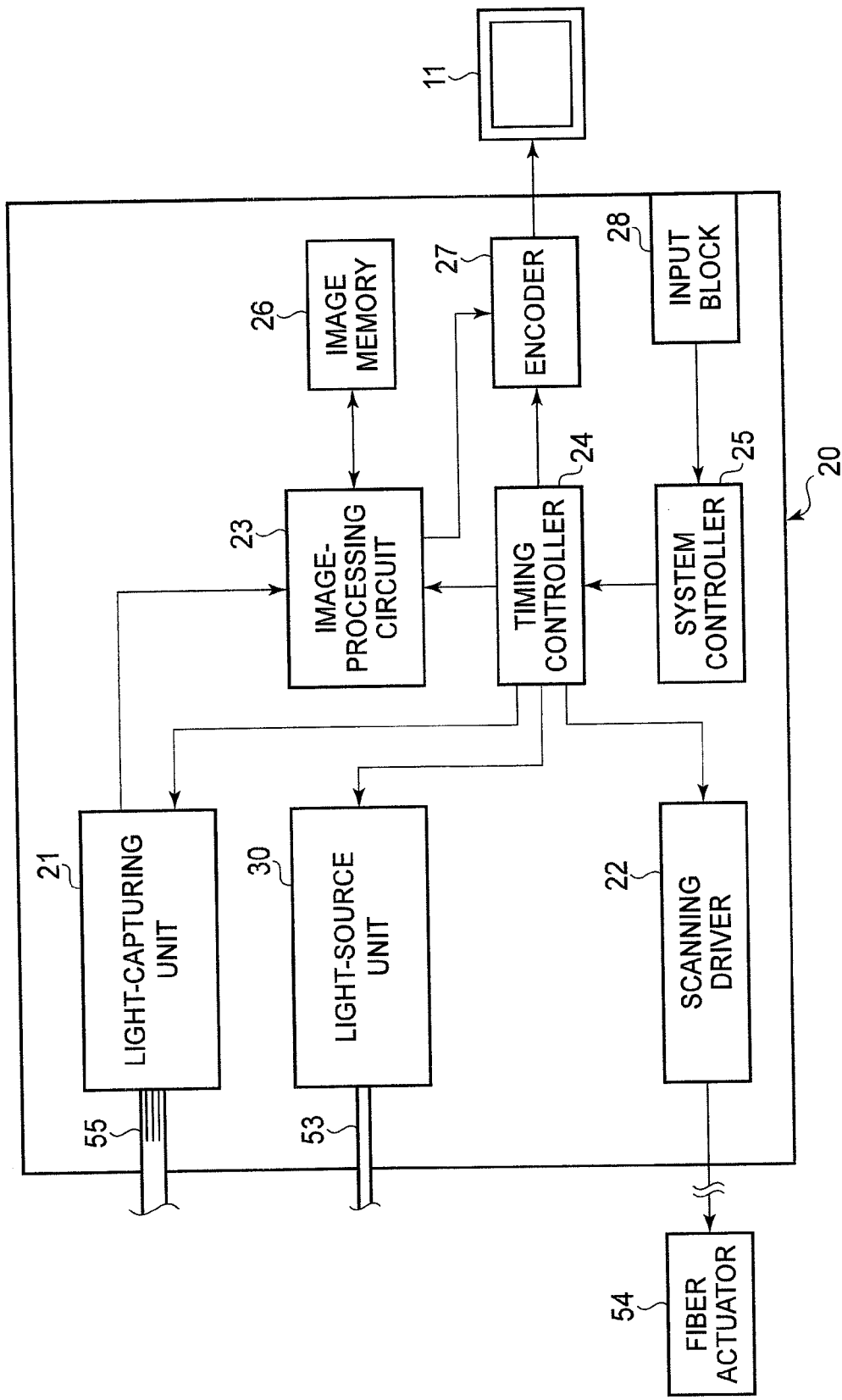
FIG. 2 is a block diagram schematically showing the internal structure of the scanning endoscope processor.

As shown in FIG. 2, the scanning endoscope processor 20 comprises a light-source unit 30, a light-capturing unit 21, a scanning driver 22, an image-processing circuit 23, a timing controller 24, a system controller 25, and other components.

The light-source unit 30 comprises red, green, and blue lasers (not depicted) that emit red, green, and blue laser beams, respectively. The red, green, and blue laser beams are mixed into white light, which is emitted from the light-source unit 30.

The white light emitted from the light-source unit 30 is supplied to the illumination fiber 53. The scanning driver 22 controls the fiber actuator 54 so that the movements of the emission end of the illumination fiber 53 follow a predetermined course.

The reflected light at the illuminated point within the observation area is transmitted to the scanning endoscope processor 20 by the image fibers 55 mounted in the scanning endoscope 50. The transmitted light is made incident on the light-capturing unit 21.

The light-capturing unit 21 generates a pixel signal according to the amount of the transmitted light. The pixel signal is transmitted to the image-processing circuit 23, which stores the received pixel signal in the image memory 26. Once pixel signals corresponding to the illuminated points dispersed throughout the observation area have been stored, the image-processing circuit 23 carries out predetermined image processing on the pixel signals, and then one frame of the image signal is transmitted to the monitor 11 via the encoder 27.

By connecting the scanning endoscope 50 to the scanning endoscope processor 20, optical connections are made between the light-source unit 30 and the illumination fiber 53 mounted in the scanning endoscope 50, and between the light-capturing unit 21 and the image fibers 55. In addition, by connecting the scanning endoscope 50 to the scanning endoscope processor 20, the fiber actuator 54 mounted in the scanning endoscope 50 is electrically connected to the scanning driver 22.

The timing for carrying out the operations of the light-source unit 30, the light-capturing unit 21, the scanning driver 22, the image-processing circuit 23, and the encoder 27 is controlled by the timing controller 24. In addition, the timing controller 24 and other components of the endoscope apparatus 10 are controlled by the system controller 25. A user can input some commands to the input block 28, which comprises a front panel (not depicted) and other mechanisms.

Figure 3:
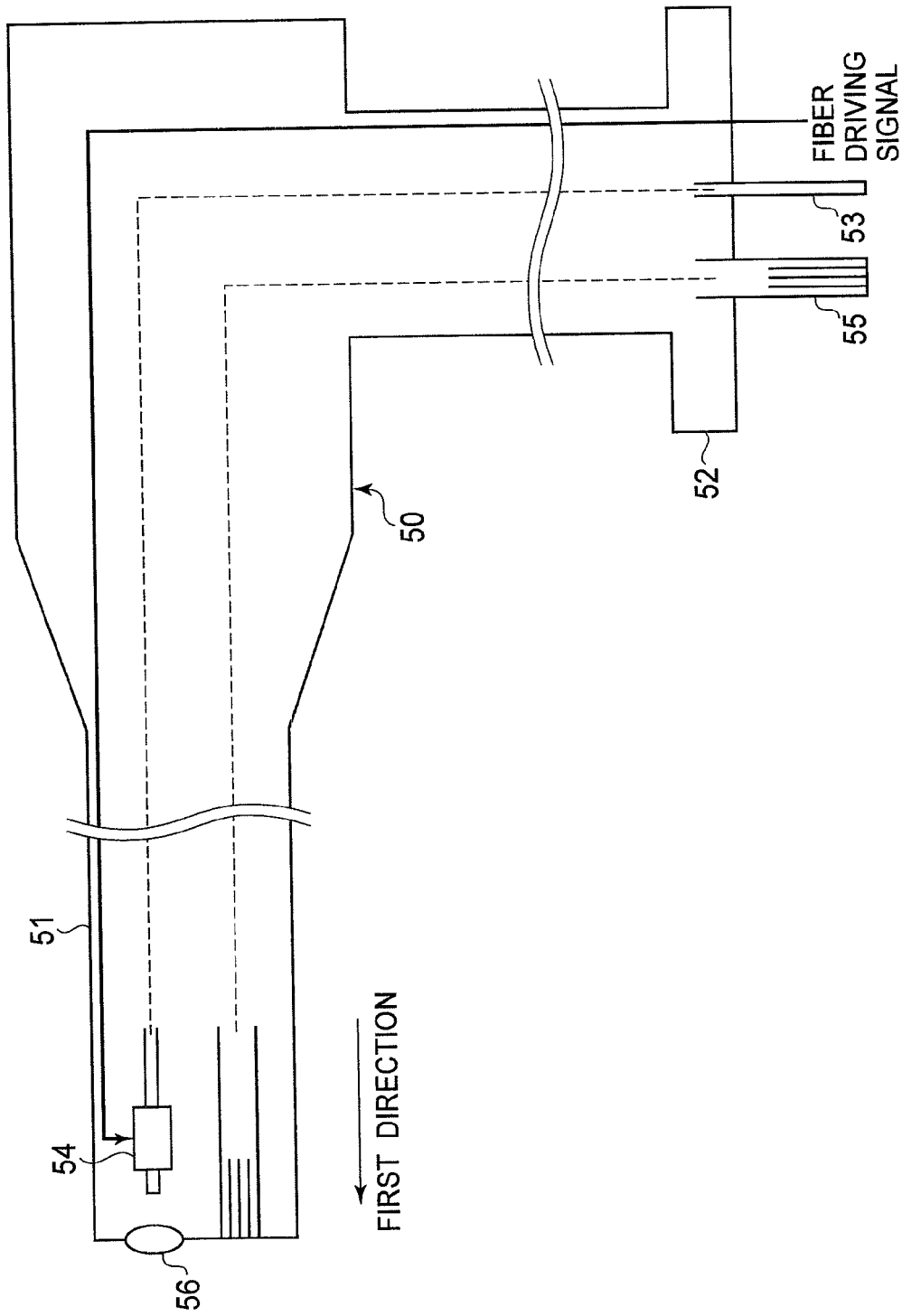
FIG. 3 is a block diagram schematically showing the internal structure of the scanning endoscope of the first embodiment.

Next, the structure of the scanning endoscope 50 is explained. As shown in FIG. 3, the scanning endoscope 50 comprises the illumination fiber 53, the fiber actuator 54, the image fibers 55, a lens 56 and other components.

The illumination fiber 53 and the image fibers 55 are arranged inside the scanning endoscope 50 from the connector 52 to the distal end of the insertion tube 51. As described above, a laser beam of the white light emitted by the light-source unit 30 is incident on the incident end of the illumination fiber 53. The incident white light is transmitted to the emission end of the illumination fiber 53.

Figure 4:
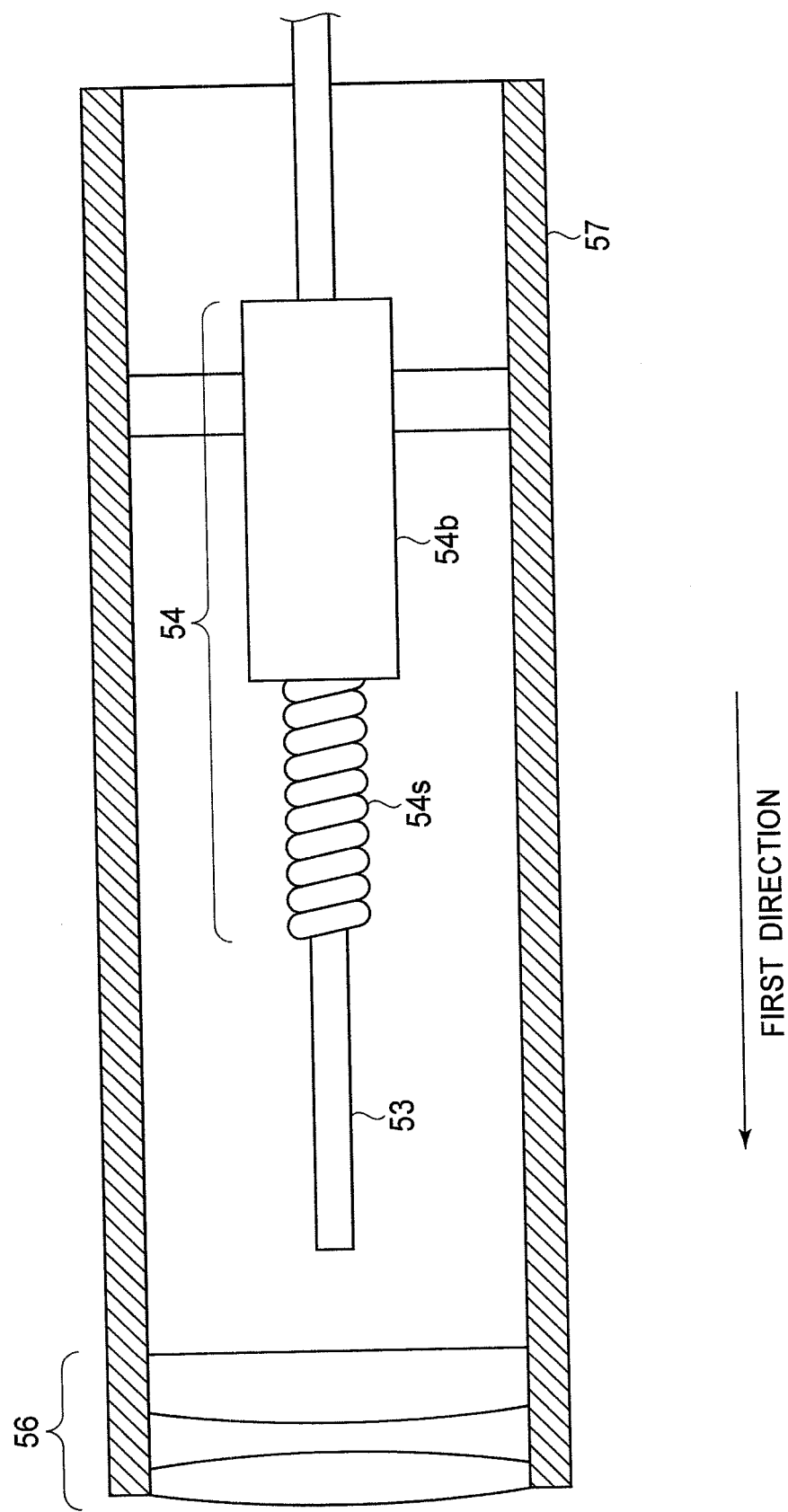
FIG. 4 is a cross-sectional view along the axial direction of the hollow tube schematically showing the structure of the fiber actuator of the first embodiment.

A solid hollow tube 57 is mounted at the distal end of the insertion tube 51 (see FIG. 4). The hollow tube 57 is positioned so that the axial direction of the distal end of the insertion tube 51 is parallel to a first direction that is an axial direction of the hollow tube 57.

The illumination fiber 53 is supported inside the hollow tube 57 by the fiber actuator 54. The illumination fiber 53 is positioned in the hollow tube 57 so that the axial direction of the hollow tube 57 is parallel to a longitudinal direction of the insertion tube 51 that is not moved by the fiber actuator 54.

Figure 5:
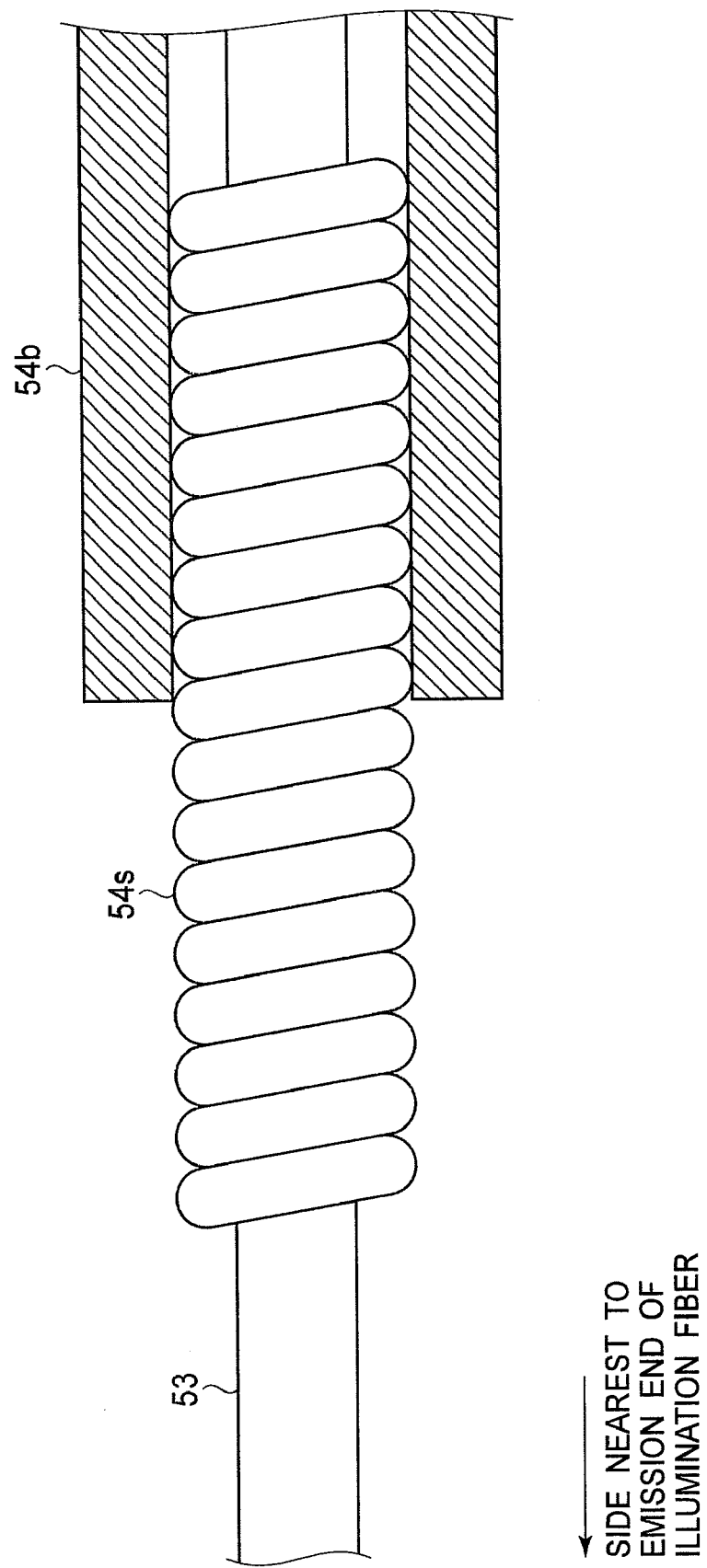
FIG. 5 is a cross-sectional view along the axial direction of the bending block schematically showing the structure of the fiber actuator of the first embodiment.

The fiber actuator 54 comprises a supporting block 54s (force transmitter) and a bending block 54b (actuator). As shown in FIG. 5, the bending block 54b is shaped cylindrically. The supporting block 54s is a metal coil spring with dimensions so that the outside and inside diameters of the coil spring are substantially equal to the inside diameter of the cylindrical bending block 54b and the outside diameter of the illumination fiber 53, respectively.

The illumination fiber 53 is inserted through the hollow interior of the coil-shaped supporting block 54s. The illumination fiber 53 is supported by the supporting block 54s as the emission end of the illumination fiber 53 protrudes from the supporting block 54s.

The supporting block 54s is inserted into the cylindrical bending block 54b. The position of the supporting block 54s is fixed in the bending block 54b so that the end of the supporting block 54s nearest to the emission end of the illumination fiber 53 protrudes from the bending block 54b. Accordingly, the supporting block 54s is positioned between the bending block 54b and the illumination fiber 53 in the radial direction.

As shown in FIG. 6, first and second bending elements 54b1 and 54b2 are fixed on the bending block 54b. The first and second bending elements 54b1 and 54b2 are pairs of two piezoelectric elements. In addition, the first and second bending elements 54b1 and 54b2 expand and contract along the axis direction of the cylindrical bending block 54b (i.e., the first direction) on the basis of a fiber driving signal transmitted from the scanning driver 22.

Two piezoelectric elements that constitute the first bending element 54b1 are fixed on the outside surface of the cylindrical bending block 54b so that the axis of the cylindrical bending block 54b is between the piezoelectric elements and so that the piezoelectric elements are linearly arranged in a second direction that is perpendicular to the first direction. In addition, two piezoelectric elements that constitute the second bending element 54b2 are fixed on the outside surface of the cylindrical bending block 54b at a location that is 90 degrees circumferentially from the first bending element 54b1 around the axis of the cylindrical bending block 54b.

Figure 7:
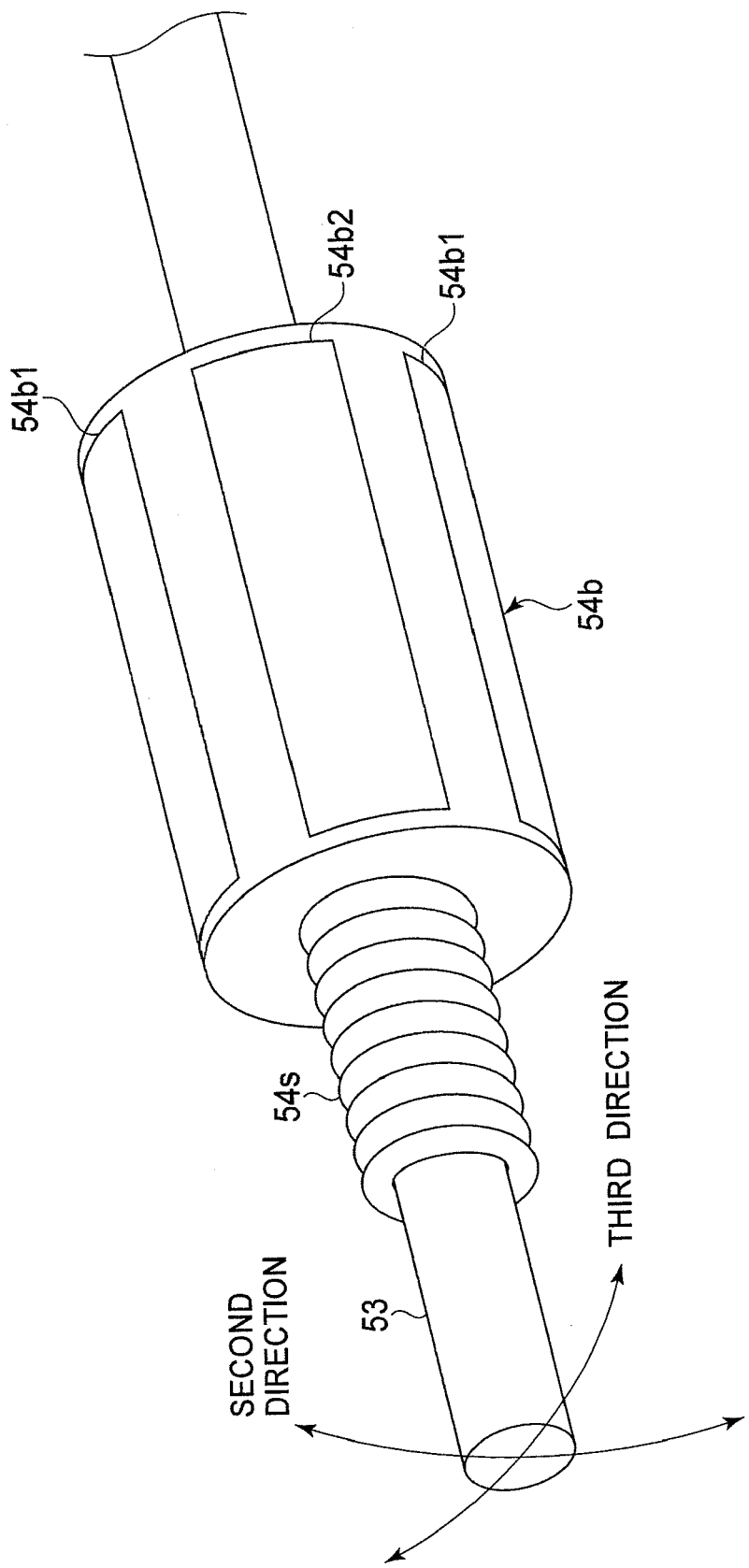
FIG. 7 is a perspective view of the fiber actuator in the first embodiment.

As shown in FIG. 7, the bending block 54b bends along the second direction by expanding one of the piezoelectric elements that constitute the first bending element 54b1 and contracting the other at the same time.

In addition, the bending block 54b bends along a third direction by expanding one of the piezoelectric elements that constitute the second bending element 54b2 and contracting the other at the same time. The piezoelectric elements constituting the second bending element 54b2 are linearly arranged in the third direction.

The illumination fiber 53 is flexible. The side of illumination fiber 53 is pushed along the second and/or third directions by the bending block 54b via the supporting block 54s (force transmitter), and the illumination fiber 53 bends toward the second and/or third directions, which are perpendicular to the longitudinal direction of the illumination fiber 53. The emission end of the illumination fiber 53 is moved by bending the illumination fiber 53.

Figure 8:
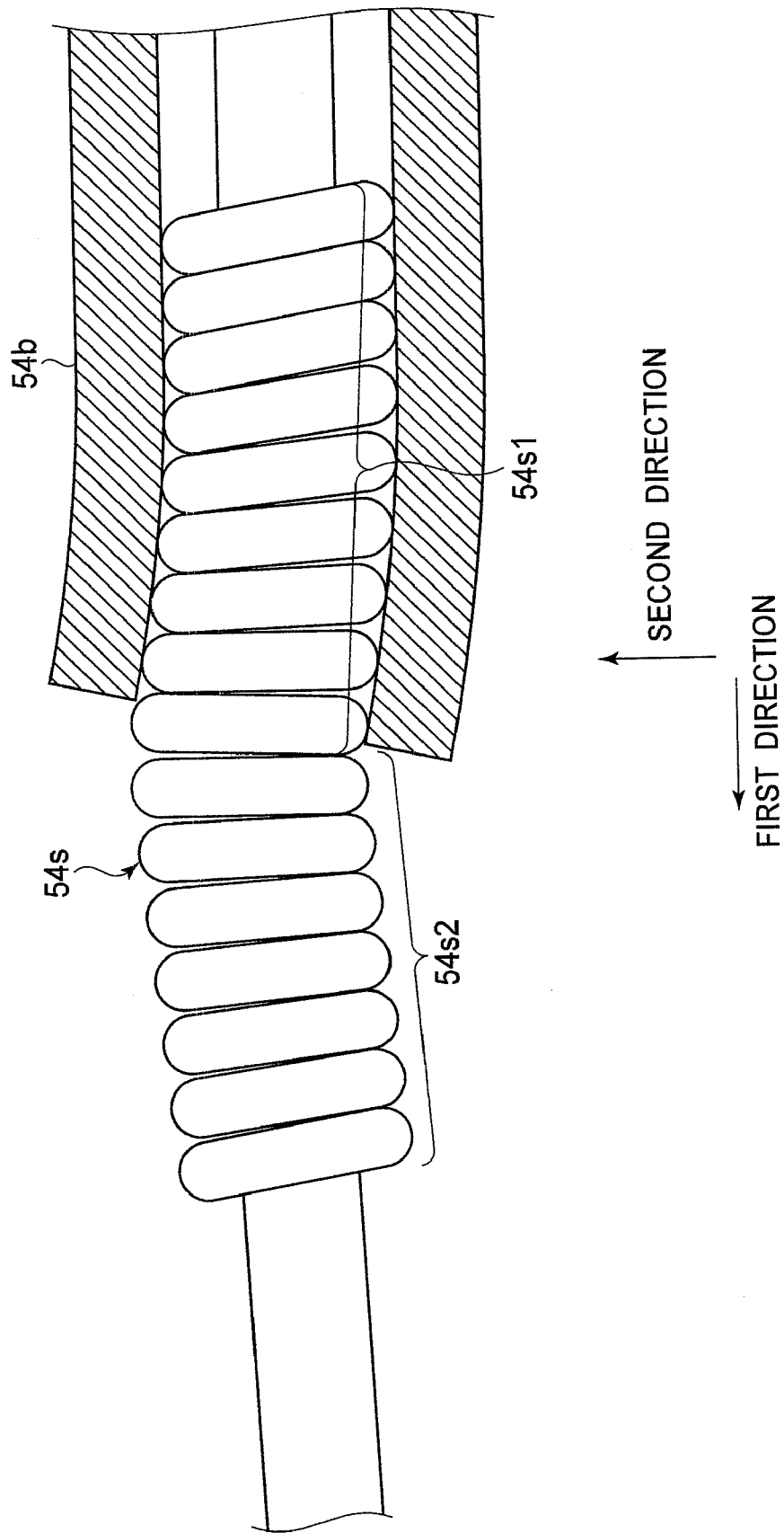
FIG. 8 is a cross-sectional view along the axial direction of the bending block illustrating the deformation of the supporting block at the moment when bending begins.

The actions of the bending block 54b pushing the side of the illumination fiber 53 is explained below. As shown in FIG. 8, when the bending block 54b bends in the second direction, a recessed section 54s1 of the supporting block 54s that is positioned entirely within (does not protrude from) the bending block 54b is pushed in the second direction.

The protruding section 54s2 of the supporting block 54s does not bend in the second direction because the pushing force exerted by the bending block 54b is not applied directly to the protruding section 54s2 of the supporting block 54s. Accordingly, the protruding section 54s2 deforms elastically and bends in the opposite direction of the second direction. Afterward, a restoring force is applied to return the protruding section 54s2 toward the second direction.

Figure 9:
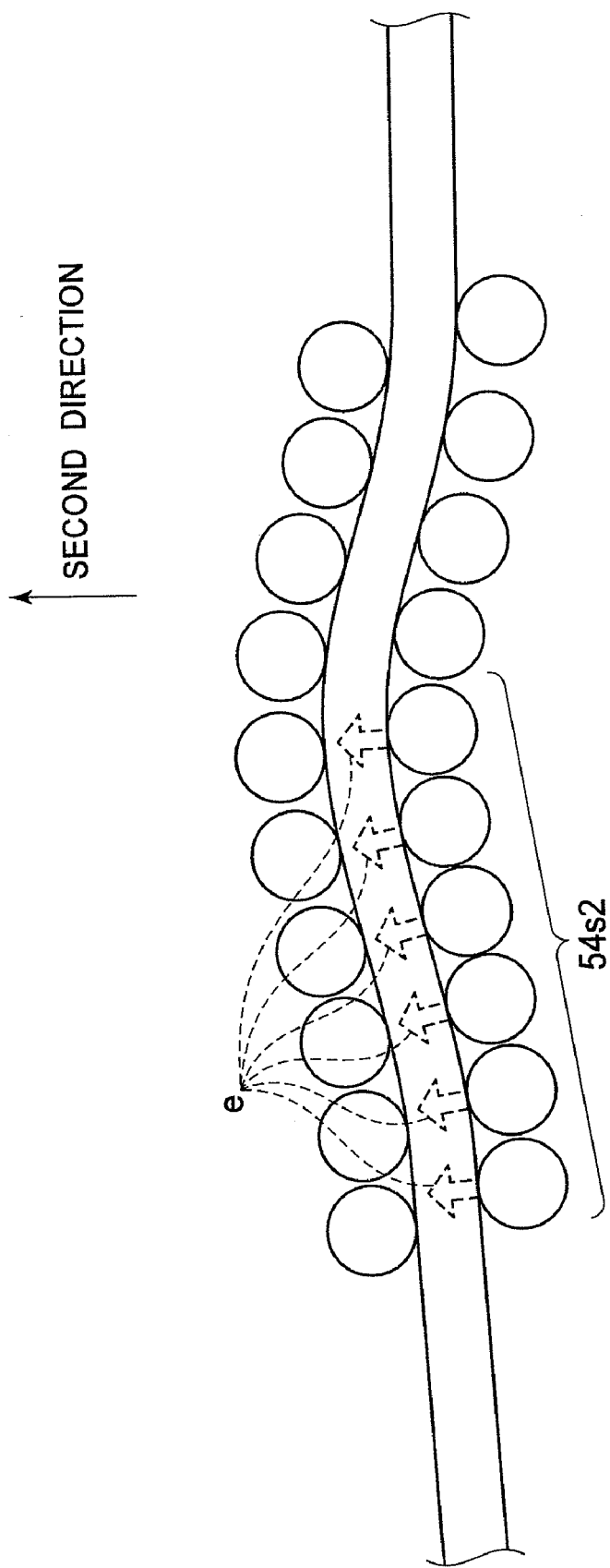
FIG. 9 is a cross-sectional view of a plane that includes a center line of the illumination fiber to illustrate the restoring force applied to the illumination fiber by the supporting block when the supporting block deforms elastically.

The outside of the illumination fiber 53 is pushed by the restoring force applied to the protruding section 54s2, which causes the illumination fiber 53 to bend along the second direction. The restoring force (see "e" in FIG. 9) is distributed across the entire protruding section 54s2 and exerted on the illumination fiber 53.

Figure 10:
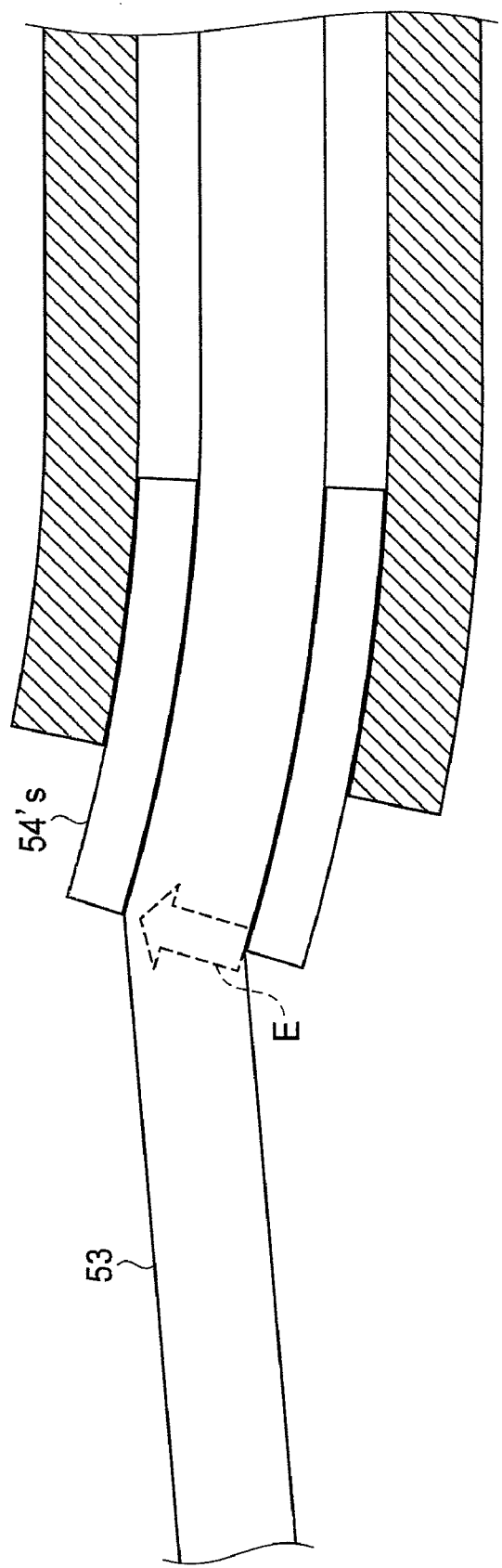
FIG. 10 is a cross-sectional view of a plane that includes a center line of the illumination fiber to illustrate the force applied to the illumination fiber by the supporting block that is assumed to be made of a solid material.

If the supporting block 54's is made of solid material, as shown in FIG. 10, a large force (see "E" in FIG. 10) is exerted on the end of the supporting block 54's where the supporting block 54's makes contact with the illumination fiber 53. The large force applied to a narrow section of the illumination fiber 53 may cause damage to the illumination fiber 53. On the other hand, in this embodiment damage of the illumination fiber 53 can be decreased by applying the restoring force distributed across the entire protruding section 54s2.

Figure 11:
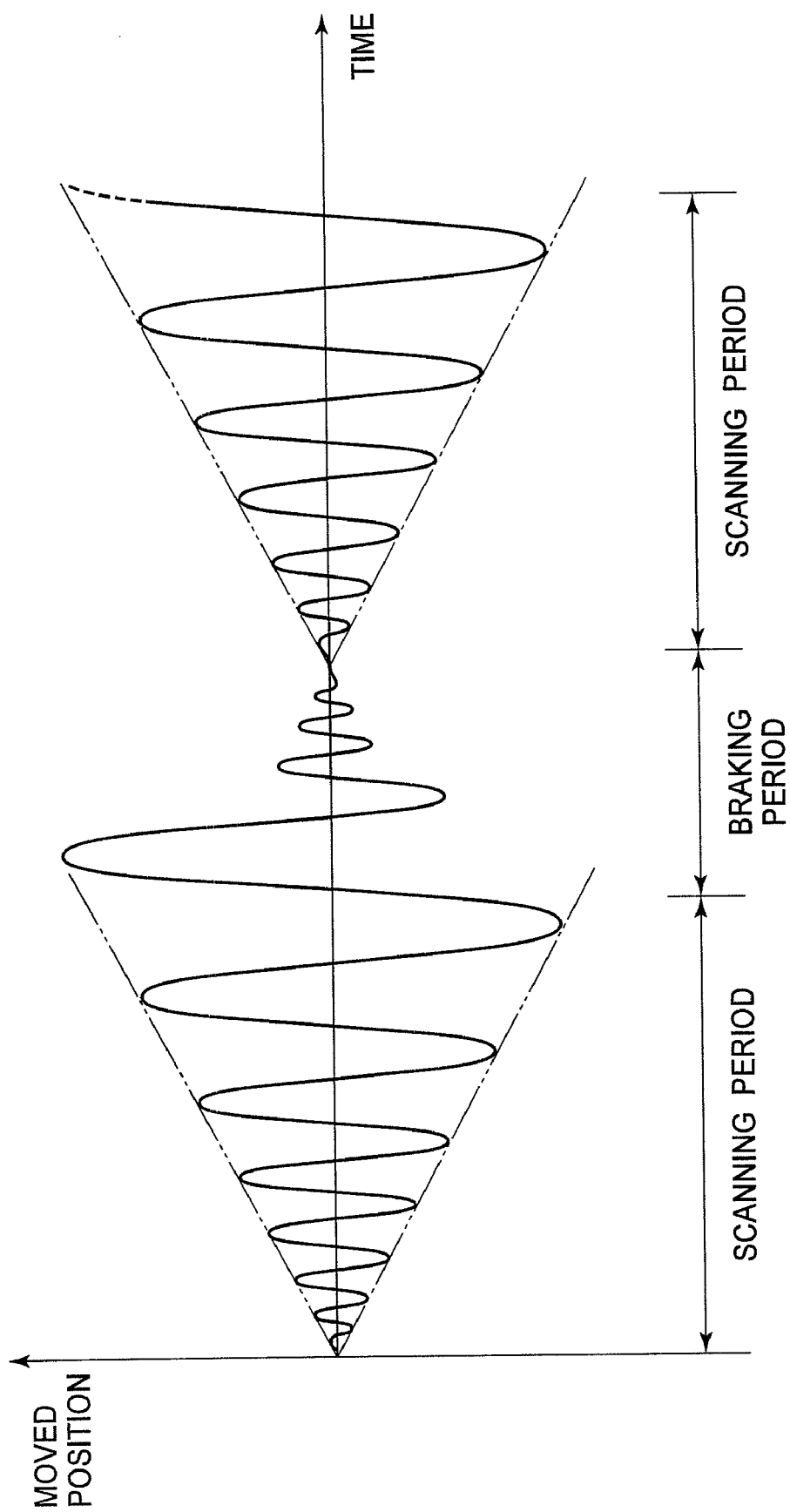
FIG. 11 is a graph illustrating the changing position of the emission end in the second and third directions.

As shown in FIG. 11, the emission end of the illumination fiber 53 is moved so that the emission end vibrates along the second and third directions at amplitudes that are repetitively increased and decreased. The frequencies of the vibration along the second and third directions are adjusted to be equal. In addition, the period to increase and to decrease the amplitudes of the vibration along the second and third directions are synchronized. Further, phases of the vibration along the second and third directions are shifted by 90 degrees.

Figure 12:
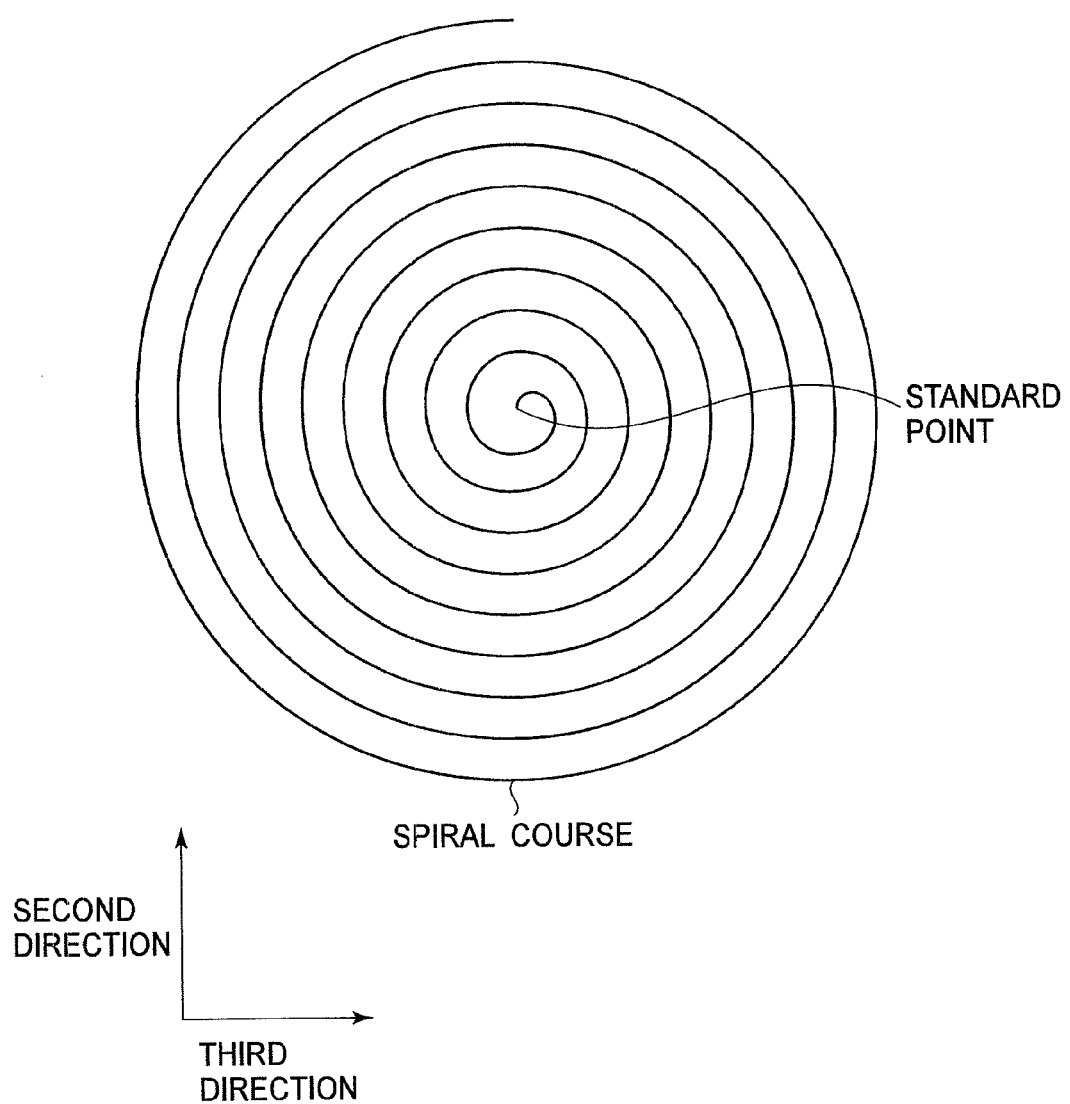
FIG. 12 illustrates a spiral course along which the emission end of the illumination fiber is moved by the fiber actuator.

By vibrating the emission end of the illumination fiber 53 along the second and third directions as described above, the emission end traces the spiral course shown in FIG. 12, and the observation area is scanned with the white laser beam.

The position of the emission end of the illumination fiber 53 when the illumination fiber 53 is not bent is defined as a standard point. While the emission end is vibrated with increasing amplitude starting from the standard point (see "scanning period" in FIG. 11), illumination of the observation area with the white laser beam and generation of pixel signals are carried out.

In addition, when the amplitude reaches a maximum among the predetermined range, one scanning operation for producing one image terminates. After termination of a scanning operation, the emission end of the illumination fiber 53 is returned to the standard point by vibrating the emission end with progressively decreasing amplitudes (see "braking period" in FIG. 11). When the emission end is returned to the standard point, it is the beginning of a scanning operation for generating another image.

The lens 56 is mounted in the emission direction in which light is emitted from the emission end that is positioned at the standard point (see FIG. 4). The lens 56 is fixed in the scanning endoscope 50 so that an optical axis of the lens 56 is parallel to the emission direction in which light is emitted from the emission end that is positioned at the standard point.

Figure 13:
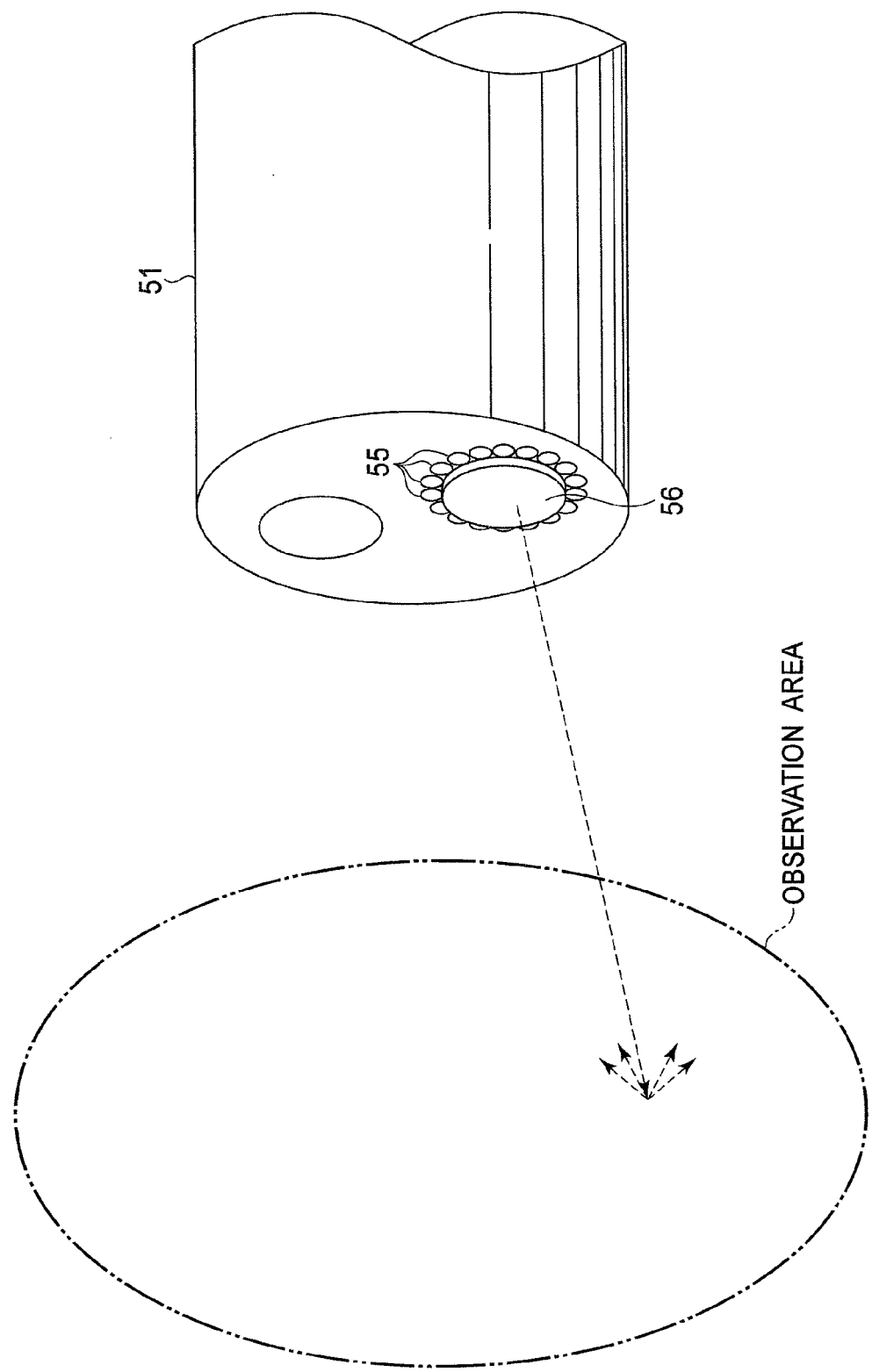
FIG. 13 illustrates the light emitted from the lens.

The white laser beam emitted from the illumination fiber 53 passes through the lens 56 before reaching an individual point within the observation area (see FIG. 13). The reflected light is scattered at that point. The scattered and reflected light is incident on the incident ends of the image fibers 55.

A plurality of the image fibers 55 are mounted in the scanning endoscope 50. The incident ends of the image fibers 55 are arranged around the lens 56 (see FIG. 13). The light that is scattered and reflected from the point in the observation area is incident on all the image fibers 55.

The reflected light incident on the incident ends of the image fibers 55 is transmitted to the emission ends of the image fibers 55. As described above, the emission ends of the image fibers 55 are optically connected to the light-capturing unit 21. The reflected light transmitted to the emission ends is incident on the light-capturing unit 21.

The light-capturing unit 21 detects the amounts of red, green, and blue light components in the reflected light, and generates pixel signals according to the amounts of the light components. The pixel signals are transmitted to the image-processing circuit 23.

The image-processing circuit 23 estimates the points where the white laser beam is shined on the basis of signals used to control the scanning driver 22. In addition, the image-processing circuit 23 stores the received pixel signals at the address of the image memory 26 that corresponds to the estimated points.

As described above, the observation area is scanned with the white laser beam, pixel signals are generated on the basis of the reflected light at the respective points illuminated with the white laser beam, and the generated pixel signals are stored at the addresses corresponding to the points. The image signal corresponding to the observation area comprises the pixel signals corresponding to the points from the scan-start point to the scan-end point. As described above, the image-processing circuit 23 carries out predetermined image processing on the image signal. After undergoing predetermined image processing, the image signal is transmitted to the monitor 11.

In the above first embodiment, it is easy to accurately manufacture a scanning endoscope with illumination fiber 53 that can sufficiently withstand the pushing force exerted by the bending block 54b.

In addition, in the above first embodiment, even if the fiber actuator 54 is exposed to a high ambient temperature, the fiber actuator 54 can still carry out a stable scanning operation, as explained below.

Although most of the light emitted from the emission end of the illumination fiber 53 passes through the lens 56, a portion of the light is reflected by the lens 56 onto the supporting block 54s. The supporting block 54s will generate heat due to the reflected light striking it. Accordingly, unless the supporting block 54s can maintain its shape without deformation when exposed to high ambient temperatures, the supporting block 54s will become distorted and carrying out a stable scanning operation will not be possible. However, in the above first embodiment, the supporting block 54s is made of metal, which provides sufficient protection against deformation caused by high ambient temperatures. Accordingly, even if the fiber actuator 54 is exposed to high ambient temperatures, the fiber actuator 54 can stably move the emission end of the illumination fiber 53 and a stable scanning operation can be carried out.

Next, a scanning endoscope of the second embodiment is explained. The primary difference between the second embodiment and the first embodiment is the shape of the supporting block. The second embodiment is explained mainly with reference to the structures that differ from those of the first embodiment. Here, the same index numbers are used for the structures that correspond to those of the first embodiment.

Figure 14:
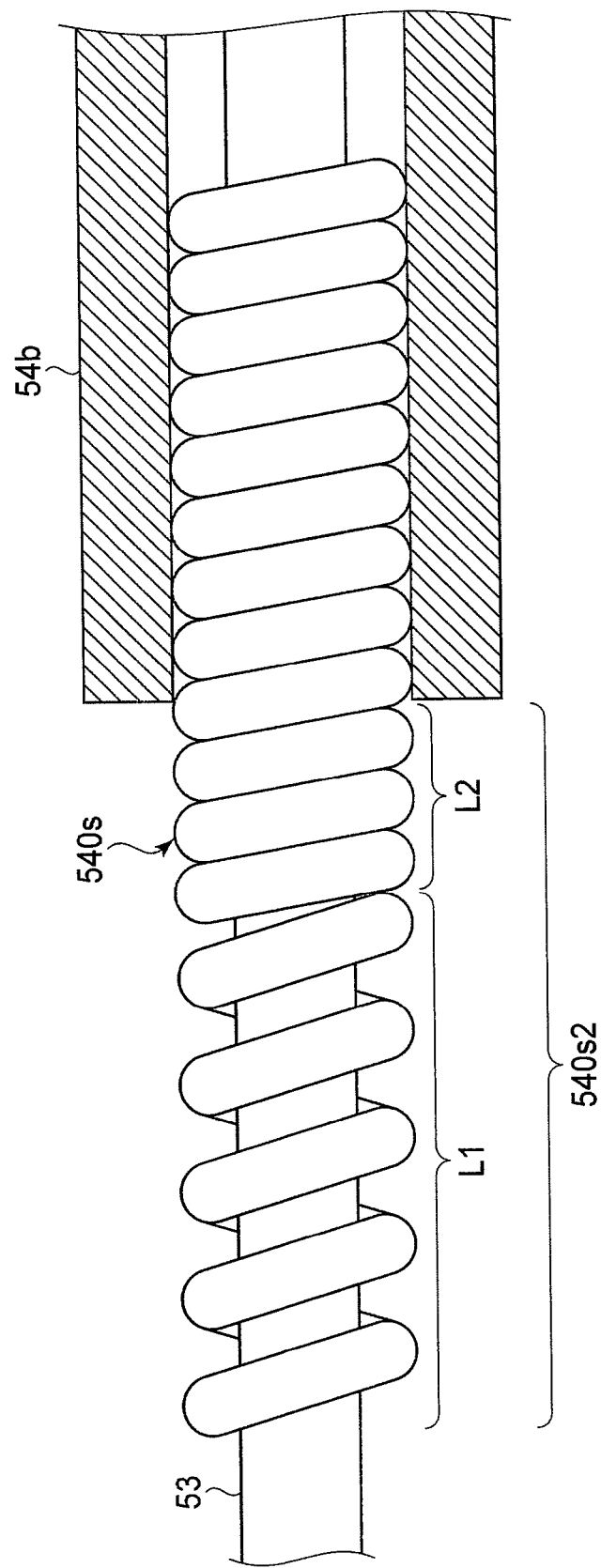
FIG. 14 is a cross-sectional view along the axial direction of the bending block schematically showing the structure of the fiber actuator of the second embodiment.

As shown in FIG. 14, the supporting block 540s is a metal coil spring configured so that the outside and inside diameters of the coil spring are substantially equal to the inside diameter of the cylindrical bending block 54b and the outside diameter of the illumination fiber 53, respectively, as in the first embodiment. However, the coil pitch of the protruding section 540s2 is not constant, unlike the first embodiment, and is relatively longer at the end nearest to the emission end of the illumination fiber 53 compared to the other end.

Owing to the above shape of the supporting block 540s, the mass per a predetermined length along the axial direction of the coil is lower at the section with the longer respective coil pitch (see "L1" in FIG. 14) than the mass of the section with the shorter coil pitch (see "L2" in FIG. 14). Accordingly, the center of mass for the combination of the illumination fiber 53 and the protruding section 540s2 is relatively closer to the bending block 54b. Owing to the shift in the center of mass, the resonant frequency of the section of the illumination fiber 53 that vibrates with the protruding section 540s2 is increased with the adjustment.

In the above second embodiment, the same effect can be achieved as in the first embodiment.

In addition, the resonant frequency of the section of the illumination fiber 53 that vibrates with the protruding section 540s2 can be adjusted to exceed the resonant frequency of the protruding section that has a constant coil pitch, unlike the first embodiment. In general, the illumination fiber 53 is oscillated at a frequency near the resonant frequency in order to achieve stable vibration. Accordingly, by adjusting the supporting block so that the resonant frequency increases, the illumination fiber 53 can be vibrated at a higher speed compared to the first embodiment.

In the prior art, the resonant frequency was adjusted by selecting a different material for the illumination fiber 53, and/or changing the length of the section of the illumination fiber 53 protruding from the fiber actuator 54. However, in the above second embodiment, the resonant frequency can be adjusted by changing the pitch of the coil and/or the position where the pitch of the coil changes, in addition to the above prior adjustment method.

Next, a scanning endoscope of the third embodiment is explained. The primary difference between the third embodiment and the first embodiment is the shape of the supporting block. The third embodiment is explained mainly with reference to the structures that differ from those of the first embodiment. Here, the same index numbers are used for the structures that correspond to those of the first embodiment.

Figure 15:
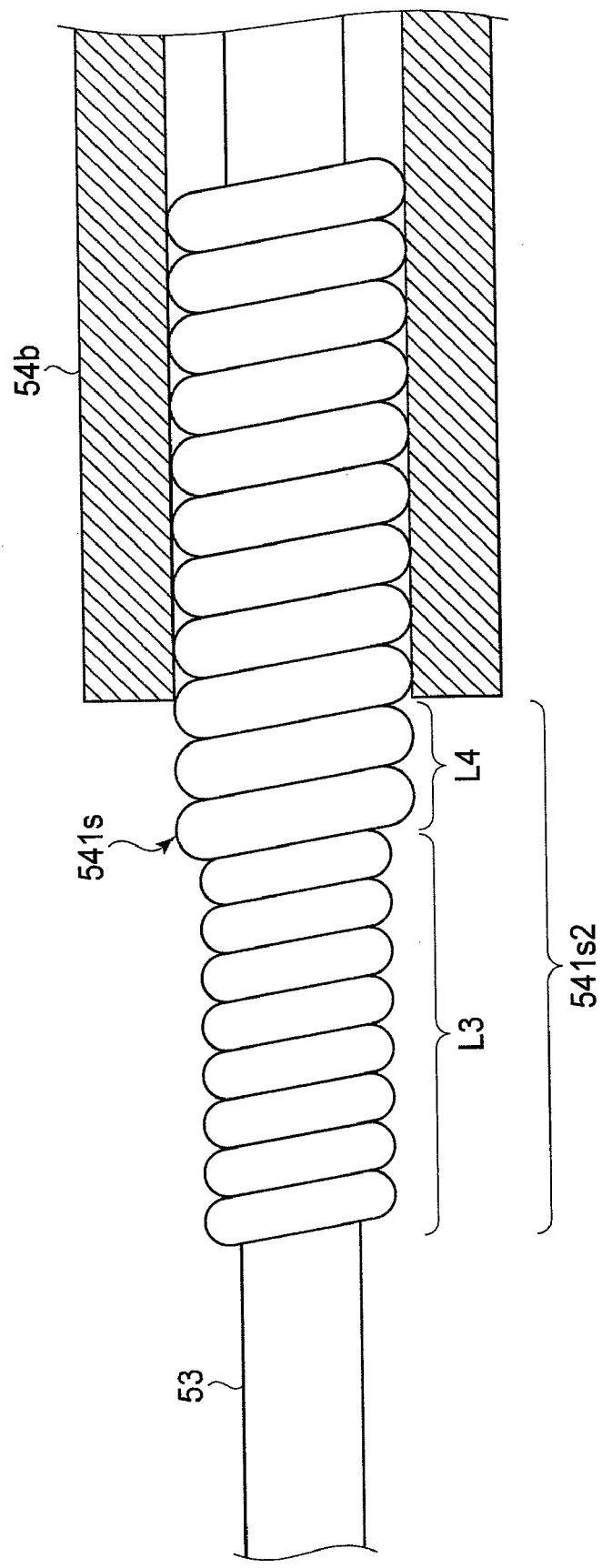
FIG. 15 is a cross-sectional view along the axial direction of the bending block schematically showing the structure of the fiber actuator of the third embodiment.

As shown in FIG. 15, the supporting block 541s is a metal coil spring configured so that the outside and inside diameters of section of the coil spring are substantially equal to the inside diameter of the cylindrical bending block 54b and the outside diameter of the illumination fiber 53, respectively, as in the first embodiment. The supporting block 541s is configured so that the diameter of the strand of the coil is not constant, with the protruding section 541s2 formed with a strand having a smaller diameter at the end nearest to the emission end of the illumination fiber 53 than at the other end, unlike the first embodiment.

Owing to the above shape of the supporting block 541s, the mass per a predetermined length along the axial direction of the spring coil is lower at the section where the strand is thinner (see "L3" in FIG. 15) than compared to the section where the strand is thicker (see "L4" in FIG. 15). Accordingly, the center of mass for the combination of the illumination fiber 53 and the protruding section 541s2 is relatively closer to the bending block 54b. Owing to the shift in the center of mass, the resonant frequency of the section of the illumination fiber 53 that vibrates with the protruding section 541s2 is increased with the adjustment.

In the above third embodiment, the same effect can be achieved as in the first embodiment. In addition, the resonant frequency of the section of the illumination fiber 53 that vibrates with the protruding section 541s2 can be adjusted to be greater than that of the protruding section where the diameter of the strand is constant, as in the second embodiment.

Next, a scanning endoscope of the fourth embodiment is explained. The primary difference between the fourth embodiment and the first embodiment is the shape of the supporting block. The fourth embodiment is explained mainly with reference to the structures that differ from those of the first embodiment. Here, the same index numbers are used for the structures that correspond to those of the first embodiment.

Figure 16:
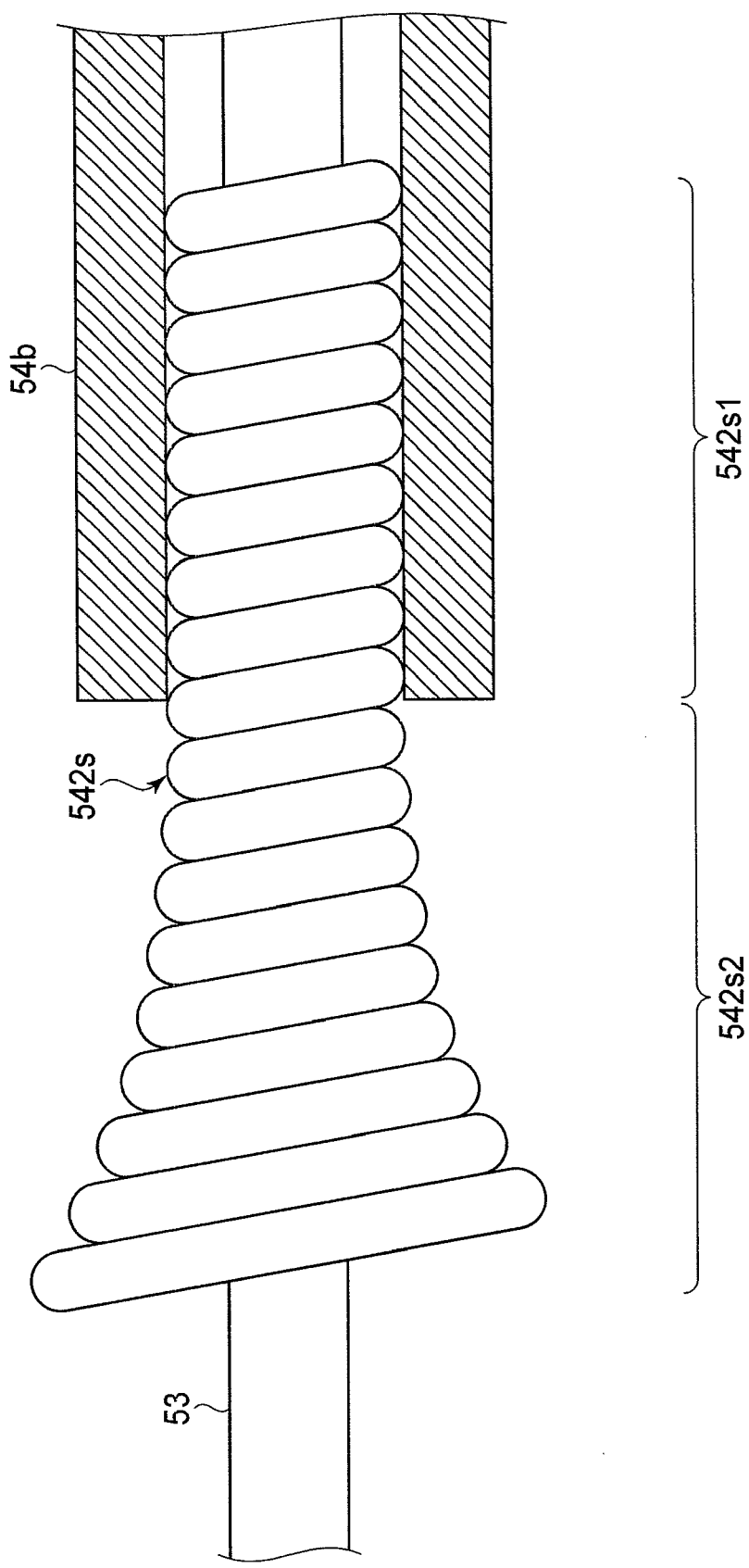
FIG. 16 is a cross-sectional view along the axial direction of the bending block schematically showing the structure of the fiber actuator of the fourth embodiment.

As shown in FIG. 16, the supporting block 542s is a metal coil spring that comprises a recessed section 542s1 and a protruding section 542s2.

The protruding section 542s2 is configured so that the outside and inside diameter of the coil spring increases as the position along the axial direction is closer to the emission end of the illumination fiber 53. In addition, the protruding section 542s2 is configured so that the distance between the centerline of the coil strand and the axial line of the supporting block increase gradually with positive convexity.

In addition, the recessed section 542s1 is configured so that the outside and inside diameter of the coil spring are substantially equal to the inside diameter of the cylindrical bending block 54b and the outside diameter of the illumination fiber 53, respectively.

Owing to the above shape of the supporting block 542s, the durability of the illumination fiber 53 can be improved relative to the first embodiment. As described above, owing to the configuration of the supporting block 54s as a coil spring, a restoring force is distributed across the entire side of the protruding section 54s2.

Figure 17:
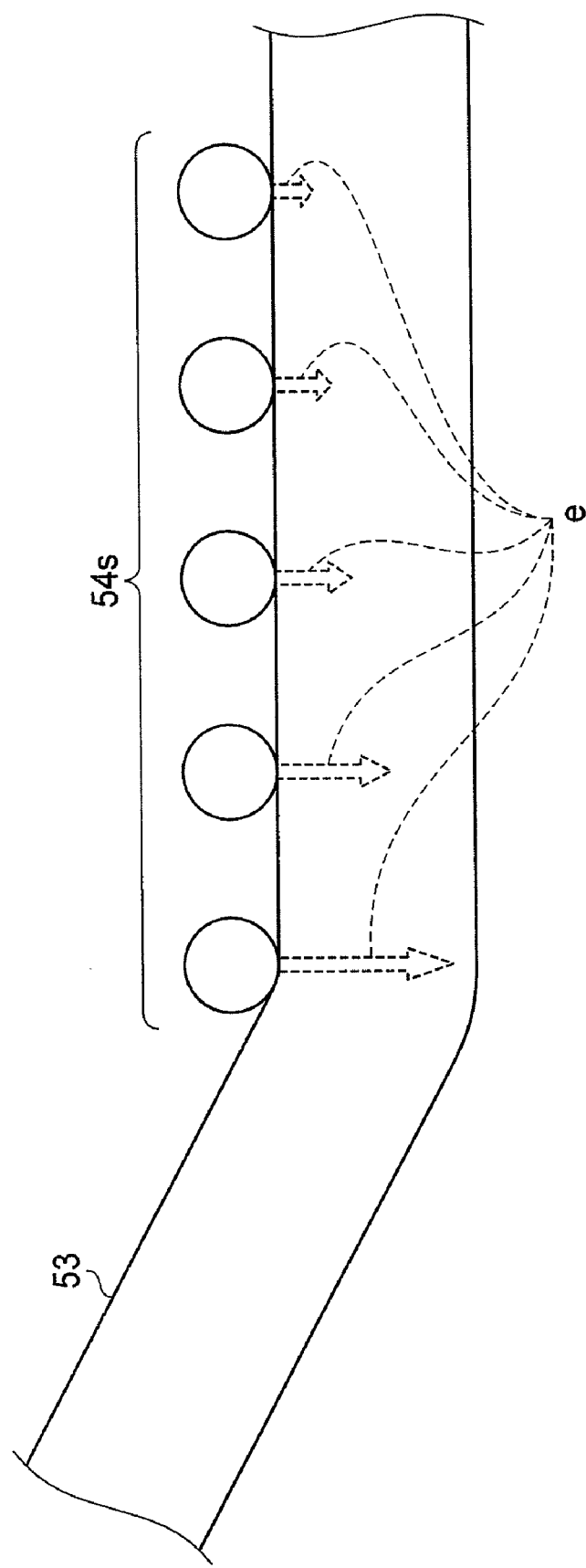
FIG. 17 is a conceptual view of the intensities of the dispersed restoring forces applied to the side of the illumination fiber in the first embodiment.
Figure 18:
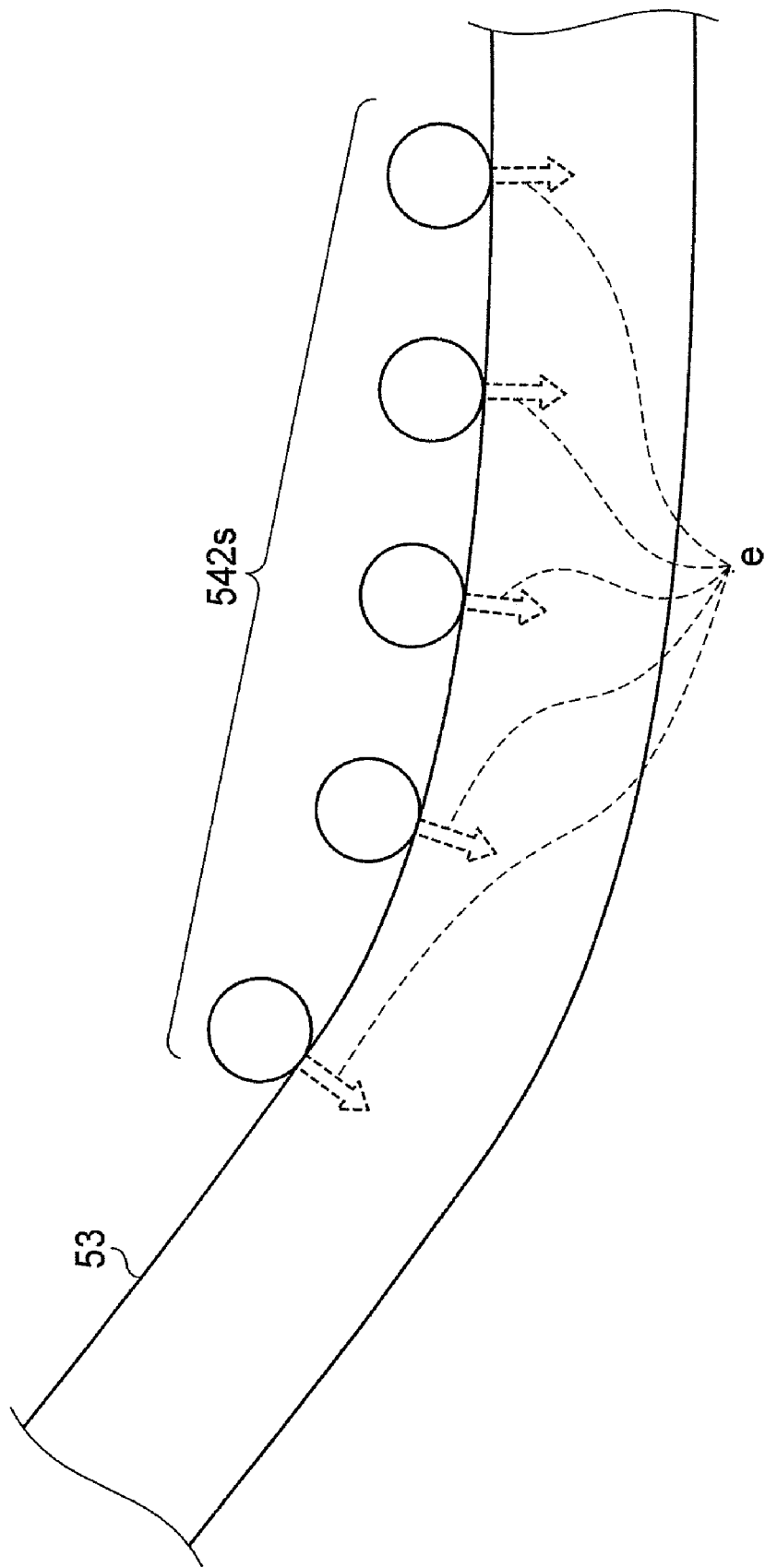
FIG. 18 is a conceptual view of the intensities of the dispersed restoring forces applied to the side of the illumination fiber in the fourth embodiment.

However, even if the restoring force is broadly distributed, the distributed restoring forces are not equal for each point where the illumination fiber 53 and the supporting block 54s make contact, and the restoring forces become greater the closer they are to the end of the supporting block 54s that is closest to the emission end of the illumination fiber 53 (see in FIG. 17). Accordingly, the greatest force among the distributed restoring forces is exerted on the illumination fiber 53 at the end of the supporting block 54s. On the other hand, in the above fourth embodiment, the illumination fiber 53 is bent along the inside surface of the protruding section 542s2, where the inside diameter gradually spreads from the recessed section 542s1 to the end, and the restoring force exerted on the illumination fiber 53 is distributed more equally than in the first embodiment (see FIG. 18).

In the above fourth embodiment, the same effect can be achieved as in the first embodiment. In addition, the durability of the illumination fiber 53 can be improved with respect to the first embodiment.

Next, a scanning endoscope of the fifth embodiment is explained. The primary difference between the fifth embodiment and the first embodiment is the shape of the supporting block. The fifth embodiment is explained mainly with reference to the structures that differ from those of the first embodiment. Here, the same index numbers are used for the structures that correspond to those of the first embodiment.

Figure 19:
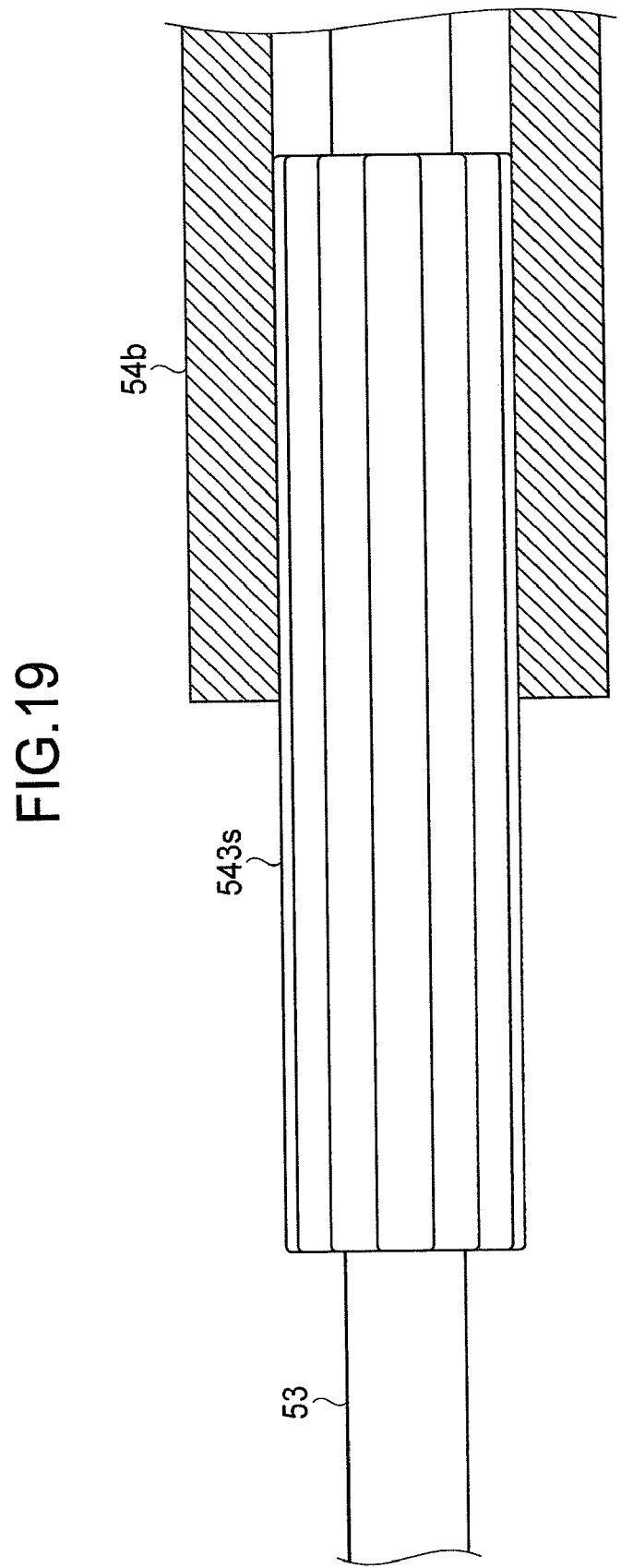
FIG. 19 is a cross-sectional view along the axial direction of the bending block schematically showing the structure of the fiber actuator of the fifth embodiment.
Figure 20:
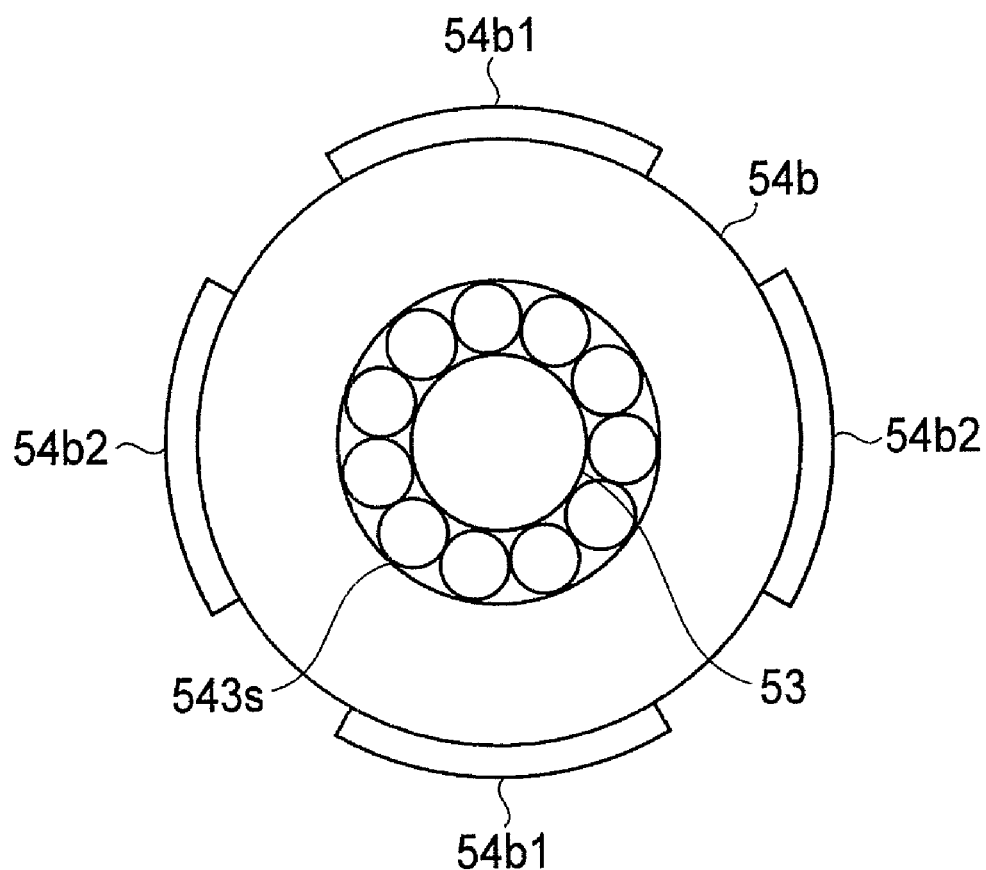
FIG. 20 is a front view of the fiber actuator in the fifth embodiment as seen from the emission end of the illumination fiber.

As shown in FIGS. 19 and 20, the supporting block 543s comprises a plurality of metal rods bundled together to form a cylinder around the illumination fiber 53. The metal rods have adequate elasticity. Accordingly, the metal rods can work the same as the coil spring in the first embodiment when the bending block 54b bends the illumination fiber 53. The illumination fiber 53 is positioned inside of the cylindrical supporting block 543s. The illumination fiber 53 is supported by the supporting block 543s as the emission end of the illumination fiber 53 protrudes from the supporting block 543s, as in the first embodiment.

In addition, a portion of the supporting block 543s is fixed inside of the cylindrical bending block 54b, as in the first embodiment. Accordingly, the supporting block 543s is positioned between the bending block 54b and the illumination fiber 53, as in the first embodiment.

In the above fifth embodiment, the same effect can be achieved as in the first embodiment.

Next, a scanning endoscope of the sixth embodiment is explained. The primary difference between the sixth embodiment and the fifth embodiment is the shape of the supporting block. The sixth embodiment is explained mainly with reference to the structures that differ from those of the fifth embodiment. Here, the same index numbers are used for the structures that correspond to those of the first embodiment.

Figure 21:
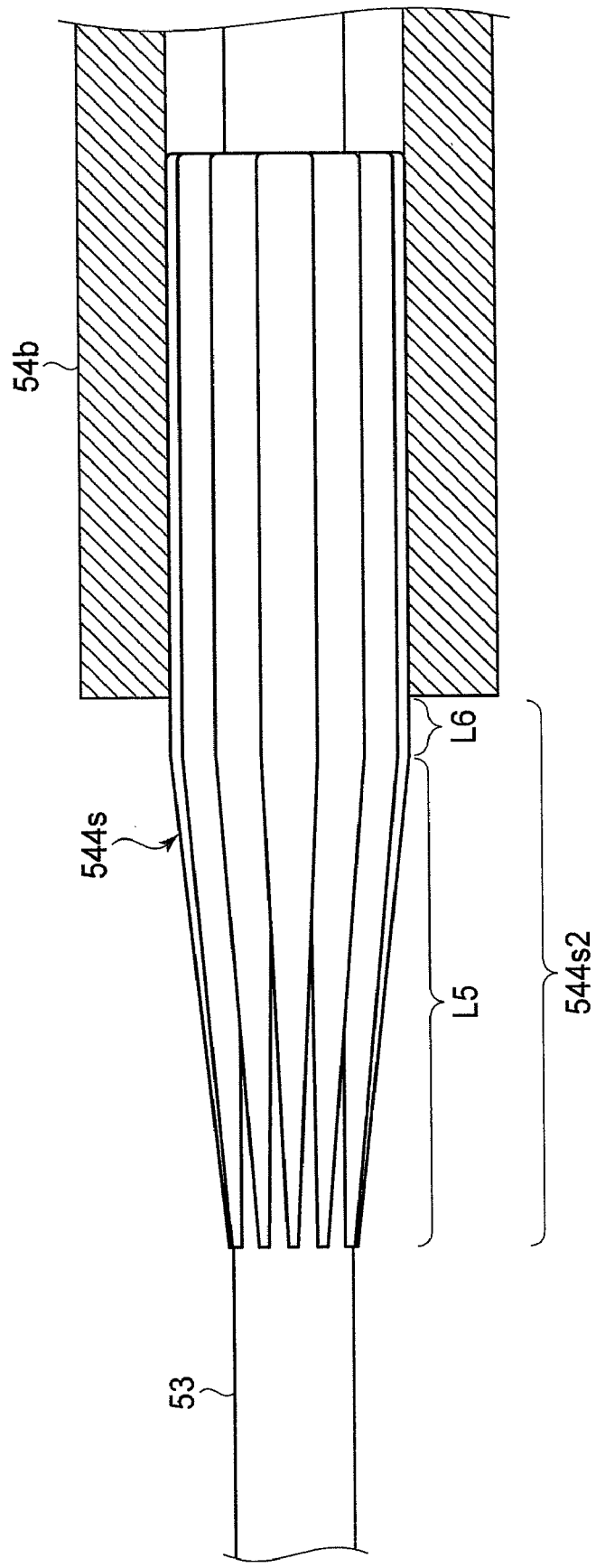
FIG. 21 is a cross-sectional view along the axial direction of the bending block schematically showing the structure of the fiber actuator of the sixth embodiment.

As shown in FIG. 21, the supporting block 544s comprises a plurality of metal rods bundled together to form a cylinder around the illumination fiber 53, as in the fifth embodiment. The rods that constitute the supporting block 544s are configured so that their thickness in the protruding section 544s2 tapers off and their diameter decreases toward the end corresponding to the emission end of the illumination fiber 53, unlike in the fifth embodiment. Accordingly, a cross-sectional area of the protruding section 544s2 perpendicular to the longitudinal direction of the protruding section 544s2 varies according to a position of the protruding section 544s2 along the first direction.

Owing to the above shape of the supporting block 544s, the mass per a predetermined length along the axial direction of the tapered section of the supporting block 544s (see "L5" in FIG. 21) is lower than that of the non-tapered, constant thickness section (see "L6" in FIG. 21). Accordingly, the center of mass for the combination of the illumination fiber 53 and the protruding section 544s2 is relatively closer to the bending block 54b. Owing to the shift in the center of mass, the resonant frequency of the section of the illumination fiber 53 vibrating with the protruding section 544s2 is increased with the adjustment.

In the above sixth embodiment, the same effect can be achieved as in the fifth embodiment. In addition, in the above sixth embodiment, the resonant frequency of the section of the illumination fiber 53 that vibrates with the protruding section 544s2 can be adjusted to be greater than that of the non-tapered, constant thickness rods constituting the supporting block, as in the second and third embodiments.

Next, a scanning endoscope of the seventh embodiment is explained. The primary difference between the seventh embodiment and the fifth embodiment is the shape of the supporting block. The seventh embodiment is explained mainly with reference to the structures that differ from those of the fifth embodiment. Here, the same index numbers are used for the structures that correspond to those of the first embodiment.

Figure 22:
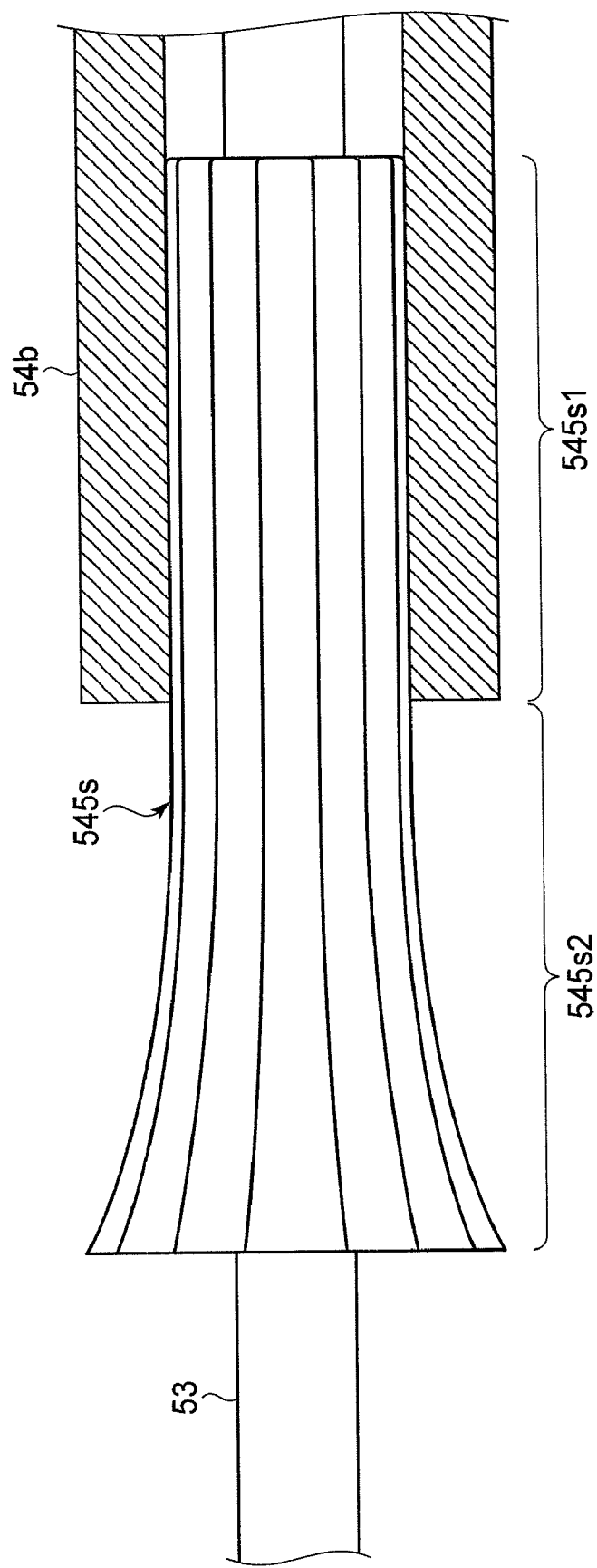
FIG. 22 is a cross-sectional view along the axial direction of the bending block schematically showing the structure of the fiber actuator of the seventh embodiment.

As shown in FIG. 22, the supporting block 545s comprises a plurality of metal rods bundled together to form a cylinder around the illumination fiber 53. The metal rods are configured to have the recessed section 545s1 and the protruding section 545s2 as one body. The recessed section 545s1 is formed to be straight. The protruding section 545s2 is funnel-shaped with a curved surface. In addition, the narrowest end of the protruding section 545s2 is connected to the recessed section 545s1 to form one body. In addition, the protruding section 545s2 is formed so that the distance between the inside surface and the axial line of the supporting block 545s increases with positive convexity as the point on the axial line moves further from the recessed section 545s1. One end of the supporting block 545s is positioned inside the bending block 54b.

In the above seventh embodiment, the same effect can be achieved as in the fifth embodiment. In addition, in the above seventh embodiment, as in the fourth embodiment, the durability of the illumination fiber 53 can be improved with respect to the fifth embodiment.

The supporting blocks 54s, 540s, 541s, 542s, 543s, 544s, and 545s comprise either a coil spring or elastic metal rods in the above first-seventh embodiments. However, other springs or elastic materials can constitute the supporting block. The same effect can be achieved as that in the first-seventh embodiments as long as the supporting block can deform elastically and transmit the restoring force to the side of the illumination fiber 53.

The fiber actuator 54b bends the illumination fiber 53 in four directions, which are the positive and negative components of the second and third directions, in the above first-seventh embodiments. However, the fiber actuator 54b may bend the illumination fiber 53 in any, but at least one, direction.

The supporting blocks 54s, 540s, 541s, 542s, 543s, 544s, and 545s are made of metal material in the above first-seventh embodiments. However, the supporting block can be made of another material that provides sufficient protection against deformation caused by high ambient temperatures. Or, the supporting block does not have to be made of such kind of material. Even if the supporting block does not provide sufficient protection against deformation at high ambient temperatures, a scanning endoscope can still be accurately manufactured with an illumination fiber 53 that can sufficiently withstand the pushing force exerted by the bending block 54b as in the first-seventh embodiments.

The supporting blocks 54s, 540s, 541s, 542s, 543s, 544s, and 545s protrude from the bending block 54b in the first-seventh embodiments. However, the supporting block may not be protruding. Even if the supporting block is not protruding, the same effect can be achieved as in the first-seventh embodiments as long as the supporting block deforms elastically and transmits the restoring force to the side of the illumination fiber 53.

The metal rods that constitute the supporting block 543s, 544s, and 545s are bundled together to form a complete circle around the illumination fiber 53, in the fifth-seventh embodiments. However, a minimum number of metal rods may be mounted in the direction for bending the illumination fiber 53. In the fifth-seventh embodiments, the illumination fiber 53 is bent in every combination of positive and negative second and third direction. If the illumination fiber 53 is bent in only one specific direction, the same effect can be achieved as in the fifth-seventh embodiments as long as the metal rod is mounted in the specific direction from the illumination fiber 53.

The center of mass for the combination of the illumination fiber 53 and the protruding section 540s2, 541s2, and 542s2 is adjusted toward the bending block 54b in the above second, third, and sixth embodiments. However, the position of the center of mass can be adjusted toward the emission end of the illumination fiber 53.

Figure 23:
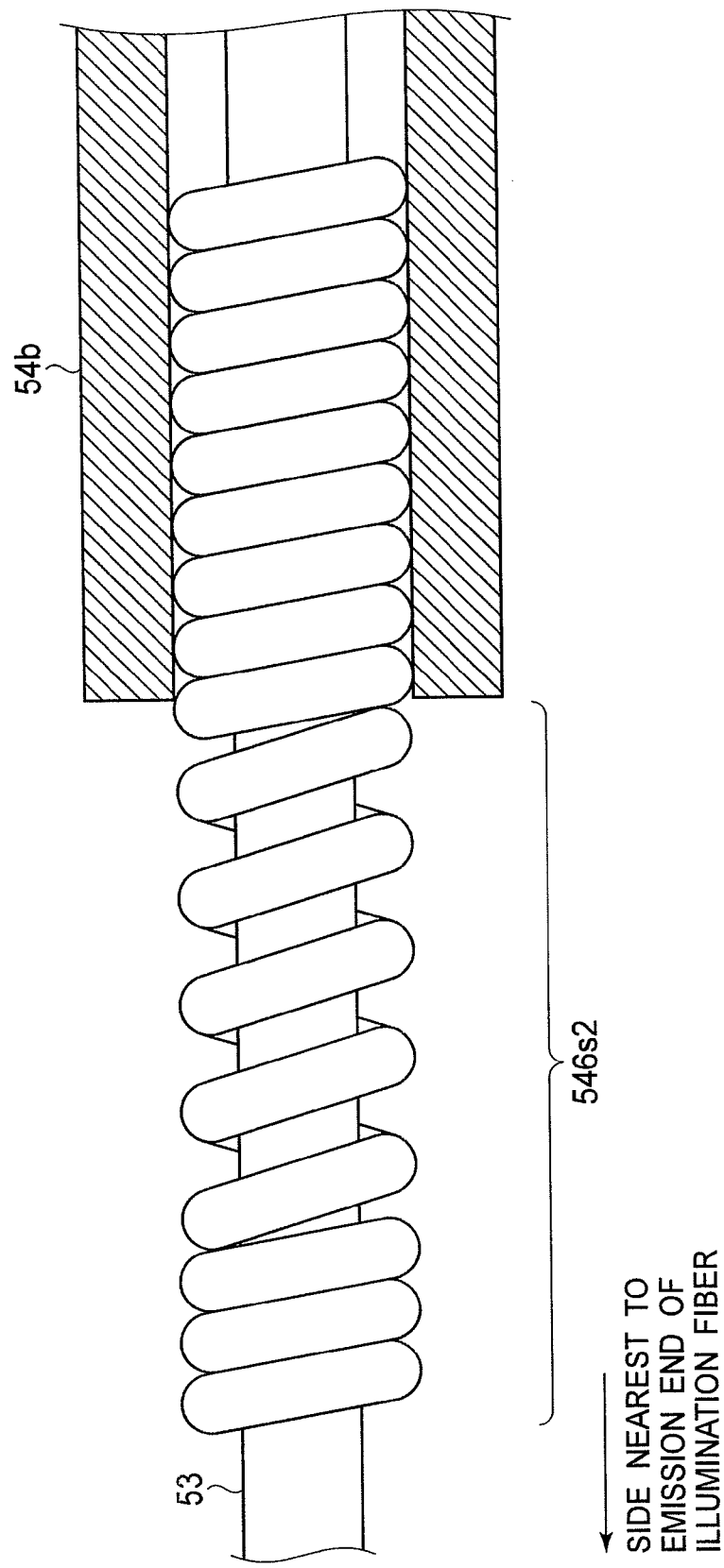
FIG. 23 is a cross-sectional view along the axial direction of the bending block schematically showing the structure of the fiber actuator with the center of mass shifted in the opposite direction of the second embodiment.

As shown in FIG. 23, the center of mass can be shifted toward the emission end of the illumination fiber 53 by forming the supporting block so that the coil pitch of the protruding section 546s2 is longer in the section nearest to the bending block 54b than the section corresponding to the side nearest to the emission end of the illumination fiber 53. By shifting the center of mass toward the emission end, the resonant frequency of the section of the illumination fiber 53 that vibrates with the protruding section can be reduced so that the illumination fiber 53 vibrates at a lower speed.

Figure 24:
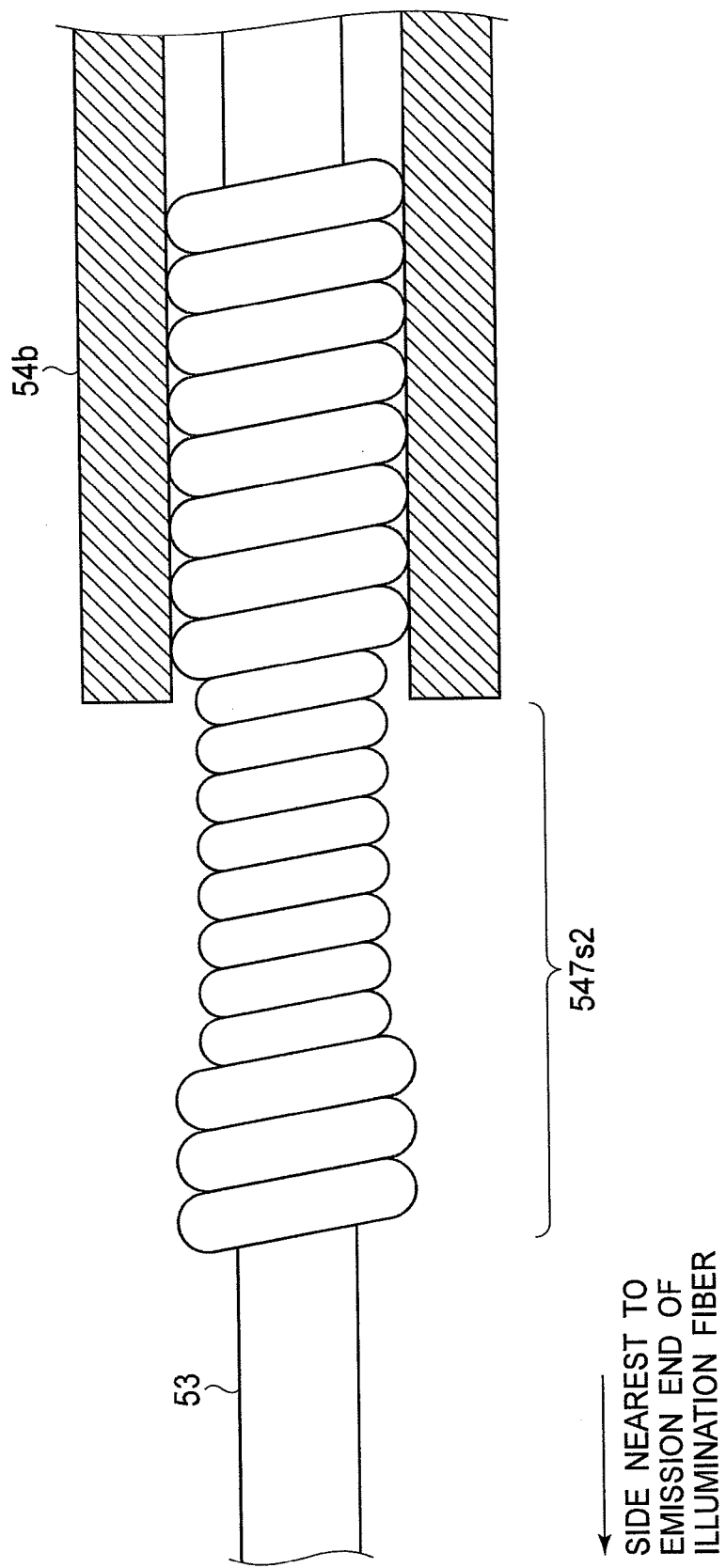
FIG. 24 is a cross-sectional view along the axial direction of the bending block schematically showing the structure of the fiber actuator with the center of mass shifted in the opposite direction of the third embodiment.

In addition, as shown in FIG. 24, the center of mass can be shifted toward the emission end of the illumination fiber 53 by configuring the supporting block so that the diameter of the strand of the protruding section 547s2 tapers off and is smallest at the end nearest to the bending block 54b.

Figure 25:
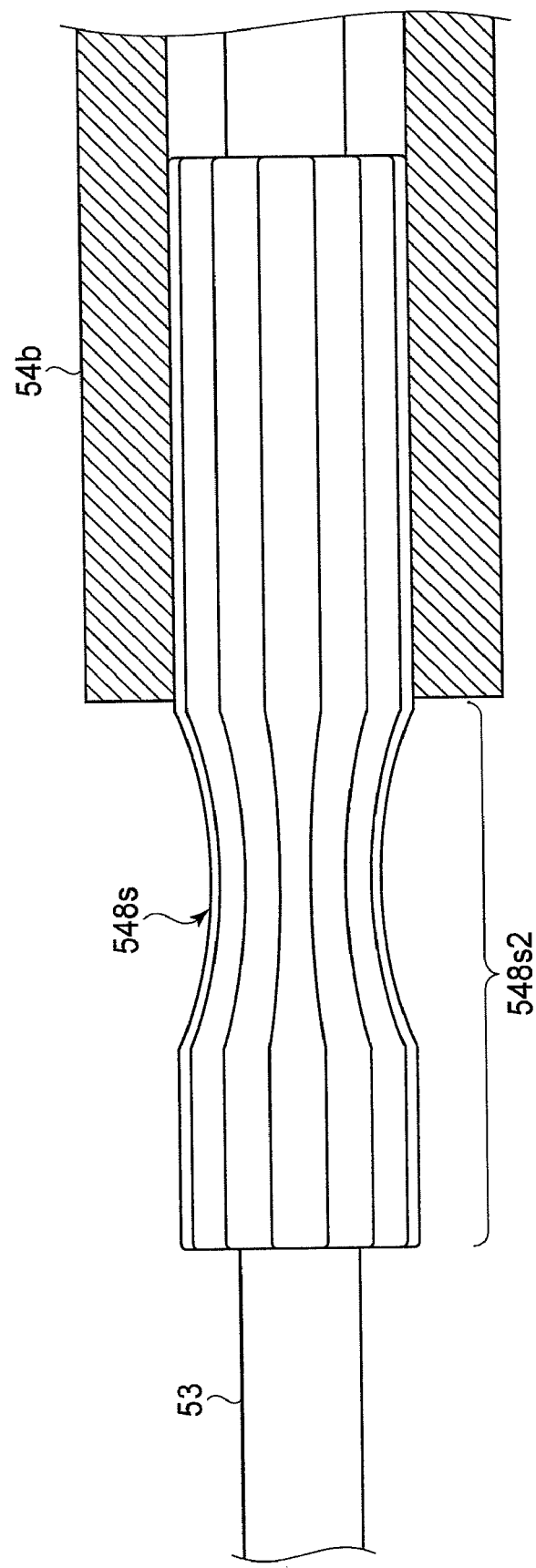
FIG. 25 is a cross-sectional view along the axial direction of the bending block schematically showing the structure of the fiber actuator with the center of mass shifted in the opposite direction of the sixth embodiment.
Figure 26:
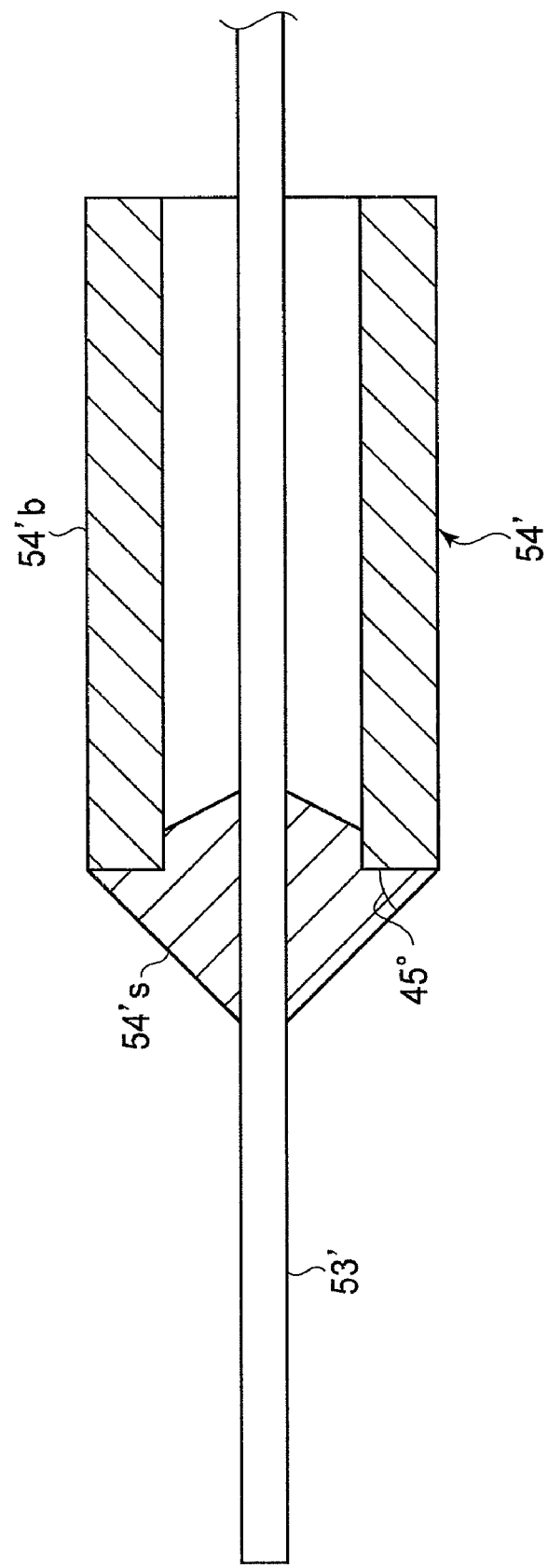
FIG. 26 is a cross-sectional view along the axial direction of the bending block schematically showing the structure of a fiber actuator in a prior art.

In addition, as shown in FIG. 25, the center of mass can be shifted toward the emission end of the illumination fiber 53 by configuring the supporting block so that the thickness of the rods that constitute the supporting block in the protruding section 548s2 tapers off and the rods become thinner toward the bending block 54b.

As described above, the center of mass is adjustable by changing the mass per a predetermined length along a longitudinal direction of the supporting block.

The supporting blocks 543s, 544s, and 545s comprise a plurality of metal rods in the fifth-seventh embodiments. However, the supporting block can comprise a plurality of flat springs.

The fiber actuator 54 moves the illumination fiber 53 so that the emission end of the illumination fiber 53 traces the predetermined spiral course, in the above first-seventh embodiments. However, the course to be traced is not limited to a spiral course. The illumination fiber 53 can be moved so that the emission end traces other predetermined courses.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2009-005109 (filed on Jan. 13, 2009), which is expressly incorporated herein, by reference, in its entirety.

The invention claimed is:

1. A scanning endoscope comprising:
a light transmitter that transmits light received at a first incident end to a first emission end, the light transmitter emitting a beam of the light exiting the first emission end, the light transmitter being flexible, a direction toward the first emission end along a longitudinal direction of the light transmitter being a first direction;
an actuator that is mounted near the first emission end, the actuator bending the light transmitter in a second direction by pushing a side of the light transmitter in the second direction, the second direction being perpendicular to the first direction; and
a force transmitter that is oriented lengthwise in the first direction, the force transmitter being elastic, the force transmitter being positioned between the light transmitter and the actuator, the force transmitter exerting a pushing force supplied by the actuator on the side of the light transmitter while the force transmitter is deformed elastically toward the first direction.

2. A scanning endoscope according to claim 1, wherein,
the actuator bends the light transmitter in a direction opposite to the first direction by pushing the side of the light transmitter in the direction opposite to the first direction, and
the force transmitter exerts the pushing force supplied by the actuator on the side of the light transmitter while the force transmitter is deformed elastically toward the direction opposite to the first direction.

3. A scanning endoscope according to claim 1, wherein,
the actuator bends the light transmitter in a third direction by pushing the side of the light transmitter in the third direction, the third direction being perpendicular to the first direction, the third direction intersecting the second direction, and
the force transmitter exerts the pushing force supplied by the actuator on the side of the light transmitter while the force transmitter is deformed elastically toward the third direction.

4. A scanning endoscope according to claim 3, wherein,
the actuator bends the light transmitter in a direction opposite to the third direction by pushing the side of the light transmitter in the direction opposite to the third direction, and
the force transmitter exerts the pushing force supplied by the actuator on the side of the light transmitter while the force transmitter is deformed elastically toward the direction opposite to the third direction.

5. A scanning endoscope according to claim 1, wherein the force transmitter is metal.

6. A scanning endoscope according to claim 1, wherein the force transmitter protrudes from the actuator toward the first direction, and the first emission end protrudes from the force transmitter toward the first direction.

7. A scanning endoscope according to claim 6, wherein a section of the force transmitter that protrudes from the actuator is a protruding section, and the shortest distance connecting two points on the light transmitter and the protruding section increases as the point on the light transmitter is moved in the first direction.

8. A scanning endoscope according to claim 6, wherein a mass of the protruding section per a predetermined length in the first direction is different at different positions in the first direction.

9. A scanning endoscope according to claim 1, wherein the force transmitter comprises a spring covering the outside of the light transmitter.

10. A scanning endoscope according to claim 9, wherein the spring protrudes from the actuator toward the first direction, and the first emission end protrudes from the spring toward the first direction.

11. A scanning endoscope according to claim 10, wherein a section of the spring that protrudes from the actuator is a protruding section, and the shortest distance connecting two points on the light transmitter and the protruding section increases as the point on the light transmitter is moved in the first direction.

12. A scanning endoscope according to claim 10, wherein a mass of the protruding section per predetermined length in the first direction is different at different positions in the first direction.

13. A scanning endoscope according to claim 9, wherein the force transmitter comprises a coil spring through which the light transmitter is inserted.

14. A scanning endoscope according to claim 13, wherein,
the coil spring protrudes from the actuator toward the first direction,
the first emission end protrudes from the coil spring toward the first direction, and
a section of the coil spring that protrudes from the actuator is a protruding section, a coil pitch of the protruding section varying according to a position of the protruding section along the first direction.

15. A scanning endoscope according to claim 13, wherein,
the coil spring protrudes from the actuator toward the first direction,
the first emission end protrudes from the coil spring toward the first direction, and
a section of the coil spring that protrudes from the actuator is a protruding section, a diameter of a strand of the protruding section varying according to a position of the protruding section along the first direction.

16. A scanning endoscope according to claim 9, wherein the force transmitter comprises a plurality of flat springs or elastic rods, the flat springs or the elastic rods being mounted around the light transmitter, the flat springs or the elastic rods being arranged so that the longitudinal direction of the flat springs or the elastic rods is parallel to the first direction.

17. A scanning endoscope according to claim 16, wherein,
the flat springs or the elastic rods protrude from the actuator toward the first direction,
the first emission end protrudes from the flat springs or the elastic rods toward the first direction, and
sections of the flat springs or the elastic rods that protrude from the actuator are protruding sections, a cross-sectional area of the protruding sections perpendicular to the longitudinal direction of the protruding sections varying according to a position of the protruding section along the first direction.

* * * * *